(12) United States Patent
Jefferies et al.

(10) Patent No.: US 9,161,992 B2
(45) Date of Patent: Oct. 20, 2015

(54) P97 FRAGMENTS WITH TRANSFER ACTIVITY

(71) Applicant: biOasis Technologies, Inc., Richmond (CA)

(72) Inventors: Wilfred Jefferies, South Surrey (CA); Mei Mei Tian, Coquitlam (CA); Timothy Vitalis, Vancouver (CA)

(73) Assignee: biOasis Technologies, Inc., British Columbia (CA)

( * ) Notice: Subject to any disclaimer, the term of this patent is extended or adjusted under 35 U.S.C. 154(b) by 0 days.

(21) Appl. No.: 14/226,506

(22) Filed: Mar. 26, 2014

(65) Prior Publication Data

US 2015/0056218 A1   Feb. 26, 2015

Related U.S. Application Data

(63) Continuation of application No. 13/566,260, filed on Aug. 3, 2012, now Pat. No. 8,722,019.

(60) Provisional application No. 61/515,792, filed on Aug. 5, 2011.

(51) Int. Cl.

| | |
|---|---|
| *A61K 47/48* | (2006.01) |
| *A61K 38/17* | (2006.01) |
| *C07K 14/705* | (2006.01) |
| *C07K 14/79* | (2006.01) |
| *C07K 16/18* | (2006.01) |
| *A61K 39/44* | (2006.01) |
| *A61K 39/395* | (2006.01) |
| *A61K 38/40* | (2006.01) |
| *A61K 38/00* | (2006.01) |

(52) U.S. Cl.
CPC ....... *A61K 47/48276* (2013.01); *A61K 38/1793* (2013.01); *A61K 38/40* (2013.01); *A61K 39/3955* (2013.01); *A61K 39/39533* (2013.01); *A61K 39/44* (2013.01); *C07K 14/70575* (2013.01); *C07K 16/18* (2013.01); *A61K 38/00* (2013.01); *C07K 14/79* (2013.01); *C07K 2319/00* (2013.01); *C07K 2319/55* (2013.01); *C07K 2319/60* (2013.01); *C07K 2319/70* (2013.01); *Y10S 977/773* (2013.01); *Y10S 977/92* (2013.01); *Y10S 977/927* (2013.01)

(58) Field of Classification Search
None
See application file for complete search history.

(56) References Cited

U.S. PATENT DOCUMENTS

| | | |
|---|---|---|
| 4,391,904 A | 7/1983 | Litman et al. |
| 4,394,448 A | 7/1983 | Szoka, Jr. et al. |
| 4,399,216 A | 8/1983 | Axel et al. |
| 4,683,195 A | 7/1987 | Mullis et al. |
| 4,683,202 A | 7/1987 | Mullis |
| 4,704,362 A | 11/1987 | Itakura et al. |
| 4,766,075 A | 8/1988 | Goeddel et al. |
| 4,784,950 A | 11/1988 | Hagen et al. |
| 4,800,159 A | 1/1989 | Mullis et al. |
| 4,801,542 A | 1/1989 | Murray et al. |
| 4,866,042 A | 9/1989 | Neuwelt |
| 4,935,349 A | 6/1990 | McKnight et al. |
| 4,946,778 A | 8/1990 | Ladner et al. |
| 5,091,513 A | 2/1992 | Huston et al. |
| 5,132,405 A | 7/1992 | Huston et al. |
| 5,186,941 A | 2/1993 | Callahan et al. |
| 5,672,683 A | 9/1997 | Friden et al. |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,844,093 A | 12/1998 | Kettleborough et al. |
| 5,962,012 A | 10/1999 | Lin et al. |
| 5,981,194 A | 11/1999 | Jefferies et al. |
| 6,015,557 A | 1/2000 | Tobinick et al. |
| 6,165,464 A | 12/2000 | Hudziak et al. |
| 6,177,077 B1 | 1/2001 | Tobinick |
| 6,261,595 B1 | 7/2001 | Stanley et al. |
| 6,387,371 B1 | 5/2002 | Hudziak et al. |
| 6,399,063 B1 | 6/2002 | Hudziak et al. |
| 6,419,934 B1 | 7/2002 | Tobinick |
| 6,419,944 B2 | 7/2002 | Tobinick |
| 6,455,494 B1 | 9/2002 | Jefferies et al. |
| 6,537,549 B2 | 3/2003 | Tobinick |
| 6,596,541 B2 | 7/2003 | Murphy et al. |
| 6,765,087 B1 | 7/2004 | Casterman et al. |
| 6,838,254 B1 | 1/2005 | Hamers et al. |
| 6,982,089 B2 | 1/2006 | Tobinick |

(Continued)

FOREIGN PATENT DOCUMENTS

| | | |
|---|---|---|
| GB | 2188637 | 10/1987 |
| WO | WO 89/04663 | 6/1989 |

(Continued)

OTHER PUBLICATIONS

International Search Report for International Application No. PCT/US2003/00894, mailed Sep. 10, 2003, 3 pages.

(Continued)

*Primary Examiner* — Amber D Steele
*Assistant Examiner* — Schuyler Milton
(74) *Attorney, Agent, or Firm* — Cooley LLP

(57) ABSTRACT

The present invention is related to fragments of human melanotransferrin (p97). In particular, this invention relates to treatment of diseases through the introduction of the melanotransferrin fragment conjugated to a therapeutic or diagnostic agent to a subject.

16 Claims, 11 Drawing Sheets

(56) References Cited

U.S. PATENT DOCUMENTS

| | | | |
|---|---|---|---|
| 7,132,511 | B2 | 11/2006 | Carr et al. |
| 7,138,371 | B2 | 11/2006 | DeFrees et al. |
| 7,179,617 | B2 | 2/2007 | DeFrees et al. |
| 7,214,658 | B2 | 5/2007 | Tobinick |
| 7,244,592 | B2 | 7/2007 | Hoogenboom et al. |
| 7,247,301 | B2 | 7/2007 | van de Winkel et al. |
| 7,462,697 | B2 | 12/2008 | Couto et al. |
| 7,595,378 | B2 | 9/2009 | van de Winkel et al. |
| 7,700,554 | B2 | 4/2010 | Beliveau et al. |
| 7,723,484 | B2 | 5/2010 | Beidler et al. |
| 7,939,072 | B2 | 5/2011 | Yarden et al. |
| 7,960,516 | B2 | 6/2011 | Matheus et al. |
| 8,546,319 | B2 | 10/2013 | Starr et al. |
| 8,722,019 | B2 | 5/2014 | Jeffries et al. |
| 2002/0119095 | A1 | 8/2002 | Gabathuler et al. |
| 2003/0072761 | A1 | 4/2003 | LeBowitz |
| 2004/0055022 | A1 | 3/2004 | Cheng et al. |
| 2004/0137557 | A1 | 7/2004 | DeFrees et al. |
| 2005/0026823 | A1 | 2/2005 | Zankel et al. |
| 2005/0158296 | A1 | 7/2005 | Starr et al. |
| 2007/0167365 | A1 | 7/2007 | Beliveau et al. |
| 2008/0014188 | A1 | 1/2008 | Zankel et al. |
| 2009/0226421 | A1 | 9/2009 | Parren et al. |
| 2010/0303797 | A1 | 12/2010 | Starr et al. |
| 2011/0093962 | A1 | 4/2011 | Heidbrink et al. |
| 2012/0107302 | A1 | 5/2012 | Berry et al. |
| 2013/0058873 | A1 | 3/2013 | Jefferies et al. |
| 2013/0183368 | A1 | 7/2013 | Hutchison et al. |
| 2014/0322132 | A1 | 10/2014 | Vitalis et al. |

FOREIGN PATENT DOCUMENTS

| | | |
|---|---|---|
| WO | WO 93/11161 | 6/1993 |
| WO | WO 94/01463 | 1/1994 |
| WO | WO 94/13804 | 6/1994 |
| WO | WO 98/23646 | 6/1998 |
| WO | WO 01/59459 | 8/2001 |
| WO | WO 02/13843 | 2/2002 |
| WO | WO 02/13873 | 2/2002 |
| WO | WO 03/009815 | 2/2003 |
| WO | WO 03/057179 | 7/2003 |
| WO | WO 2004/078215 | 9/2004 |
| WO | WO 2006/079372 | 8/2006 |
| WO | WO 2013/006706 | 1/2013 |
| WO | WO 2013/022738 | 2/2013 |
| WO | WO 2014/022515 | 2/2014 |
| WO | WO 2014/160438 | 10/2014 |

OTHER PUBLICATIONS

International Preliminary Examination Report for International Application No. PCT/US2003/00894, dated Feb. 14, 2005, 5 pages.
International Search Report and Written Opinion for International Application No. PCT/US2012/045568, mailed on Sep. 27, 2012, 9 pages.
Examination Report for Australian Application No. 2012294673, dated Sep. 16, 2014, 4 pages.
Notice of Allowance in U.S. Appl. No. 13/566,260, mailed Dec. 26, 2013, 8 pages.
Office Action in U.S. Appl. No. 13/566,260, mailed Sep. 5, 2013, 6 pages.
International Preliminary Report on Patentability for International Application No. PCT/US2012/049475, dated Feb. 11, 2014, 7 pages.
International Search Report and Written Opinion for International Application No. PCT/US2012/049475, mailed on Oct. 25, 2012, 9 pages.
Aktas, Y. et al., "Development and brain delivery of chitosan-PEG nanoparticles functionalized with the monoclonal antibody 0X26," Bioconjugate Chem,16(6):1503-1511 (2005).
Bickel, U. et al., "Pharmacologic effects in vivo in brain by vector-mediated peptide drug delivery," Proc. Natl. Acad. Sci. USA, 90(7):2618-2622 (1993).
Bickel, U. et al., "In vivo demonstration of subcellular localization of anti-transferrin receptor monoclonal antibody-colloidal gold conjugate in brain capillary endothelium," Journal of Histochemistry and Cytochemistry, 42(11):1493-1497 (1994).
Bickel, U. et al., "In vivo cleavability of a disulfide-based chimeric opioid peptide in rat brain," Bioconjugate Chem, 6(2):211-218 (1995).
Bickel, U. et al., "Delivery of peptides and proteins through the blood-brain barrier," Advanced Drug Delivery Review, 46(1-3):247-279 (2001).
Blattler, W. A. et al., "New heterobifunctional protein cross-linking reagent that forms an acid-labile link," Biochem., 24:1517-1524 (1985).
Boado, R. J. et al., "Cloning and expression in Pichia pastoris of a genetically engineered single chain antibody against the rat transferrin receptor," Journal of Drug Targeting, 8(6):403-412 (2000).
Broadwell, R. D. et al., "Transcytosis of protein through the mammalian cerebral epithelium and endothelium. III. Receptor-mediated transcytosis through the blood-brain barrier of blood-borne transferrin and antibody against the transferrin receptor," Experimental Neurology, 142(1):47-65 (1996).
Carter, P. et al., "Humanization of an anti-p185$^{HER2}$ antibody for human cancer therapy," Proc. Natl. Acad. Sci. USA, 89:4285-4289 (1992).
Cerletti, A. et al., "Endocytosis and transcytosis of an immunoliposome-based brain drug delivery system," Journal of Drug Targeting, 8(6):435-446 (2000).
Chen, Q. et al., "Efficient Synthesis of Doxorubicin Melanotransferrin p97 Conjugates Through SMCC Linker," Synthetic Communications, 34(13) (2004).
CO, M. S. et al., "Humanized antibodies for antiviral therapy," Proc. Natl. Acad. Sci. Usa, 88(7):2869-2873 (1991).
Co, M. S. et al. "Chimeric and humanized antibodies with specificity for the CD33 antigen," J. Immunol., 148(4):1149-1154 (1992).
Deguchi, Y. et al., "Retention of biologic activity of human epidermal growth factor following conjugation to a blood-brain barrier drug delivery vector via an extended poly (ethylene glycol) linker," Bioconjugate Chem., 10(1):32-37 (1999).
Delabarre, B. et al., "Central Pore Residues Mediate the p97/VCP activity required for ERAD," Molecular Cell, 19(22):451-462 (2006).
Demeule, M. et al., "High transcytosis of melanotransferrin (P97) across the blood-brain barrier," Journal of Neurochemistry, 83:924-933 (2002).
Demeule, M. et al., "Regulation of plasminogen activation: A role for melantransferrin (p97) in cell migration," Blood, 102(5):1723-1731 (2003).
Dorr, R. T. et al., "In vitro rat myocyte cardiotoxicity model for antitumor antibiotics using adenosine triphosphate/protein ratios," Cancer Research, 48:5222-5227 (1988).
Endo, N. et al., "In-Vitro Cytotoxicity of a Human Serum Albumin-mediated Conjugate of Methotrexate with Anti-MM46 Monoclonal Antibody," Cancer Research, 47(4):1076-1080 (1987).
Enzyme: L-iduronidase. EC 3.2.1.76. http://www.chem.qmul.ac.uk/iubmb/enzyme/EC3/2/1/76.html, 2 pages. (Printed Feb. 17, 2009).
Enzyme: N-acetylglucosaminidase. EC 3.2.1.96. http://www.chem.qmul.ac.uk/iubmb/enzyme/EC3/2/1/96.html, 2 pages. (Printed Feb. 17, 2009).
Enzyme: β-N-acetylhexosaminidase. EC 3.2.1.52. http://www.chem.qmul.ac.uk/iubmb/enzyme/EC3/2/1/52.html, 2 pages. (Printed Dec. 17, 2009).
Friden, P. M., "Anti-transferrin receptor antibody and antibody-drug conjugates cross the blood-brain barrier," Proc. Natl. Acad. Sci. USA, 88(11):4771-4775 (1991).
Geuze, H. J. et al., "Possible Pathways for Lysosomal Enzyme Delivery," Journal of Cell Biology, 101:2253-2262 (1985).
Gosk, S. et al., "Targeting anti-transferrin receptor antibody (OX26) and OX26-conjugated liposomes to brain capillary endothelial cells using in situ perfusion," Journal of Cerebral Blood Flow & Metabolism, 24(11):1193-1204 (2004).
Holliger, P. et al., "'Diabodies': Small bivalent and bispecific antibody fragments," Proc. Natl. Acad. Sci., 90:6444-6448 (1993).

(56) References Cited

OTHER PUBLICATIONS

Hu, S. et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res., 56:3055-3061 (1996).
Huston, J. S. et al., "Protein engineering of antibody binding sites: recovery of specific activity in an antidigoxin single-chain Fv analogue produced in *Escherichia coli*," Proc. Natl. Acad. Sci. USA, 85(16):5879-5883 (1988).
Huwyler, J. et al., "Receptor mediated delivery of daunomycin using immunoliposomes: pharmacokinetics and tissue distribution in the rat," Journal of Phamacology & Experimental Therapeutics, 282(3):1541-1546 (1997).
Inoue, T. et al., "Predictive in vitro cardiotoxicity and hepatotoxicity screening system using neonatal rat heart cells and rat hepatocytes," AATEX 14, Special Issue, Proc. 6th World Congress on Alternatives & Animal Use in the Life Sciences, pp. 457-462 (Aug. 21-25, 2007).
Jefferies, W. A. et al., "Transferrin receptor on endothelium of brain capillaries," Nature, 312:162-163 (1984).
Jefferies, W. A. et al., "Analysis of lymphopoletic stem cells with a monoclonal antibody to the rat transferrin receptor," Immunology, 54(2):333-341 (1985).
Jolly, R. D. et al., "Lysosomal storage diseases of animals: an essay in comparative pathology," Veterinary Pathology Online, 34:527-548 (1997).
Kang, Y. S. et al., "Pharmacokinetics and organ clearance of a 3'-biotinylated, internaly [32P]-labeled phosphodiester oligodeoxynucleotide coupled to a neutral avidin/monoclonal antibody conjugate," Drug Metabolism and Disposition, 23(1):55-59 (1995).
Kang, Y. S. et al., "Stability of the disulfide bond in an avidin-biotin linked chimeric peptide during in vivo transcytosis through brain endothelial cells," Journal of Drug Targeting, 8(6):425-434 (2000).
Kang, Y. S. et al., "Use of neutral avidin improves pharmacokinetics and brain delivery of biotin bound to an avidin-monoclonal antibody conjugate," Journal of Pharmacology & Experimental Therapeutics, 269(1):344-350 (1994).
Karkan, D. et al., "A Unique Carrier for Delivery of Therapeutic Compounds beyond the Blood-Brain Barrier," PLOS One, 3(6):E2469.1-E2469.14 (2008).
King, T. P. et al., "Preparation of protein conjugates via intermolecular hydrazone linkage," Biochem, 25:5774-5779 (1986).
Kurihara, A. et al., "Aβ1-40 Peptide radiopharmaceuticals for brain amyloid imaing: III-Inchelation, conjugation to poly(ethylene glycol)-biotin linkers, and autoradiography with Alzheimer's disease brain sections," Bioconjugate Chem, 11:380-386 (2000).
Moos, T. et al., "Restricted transport of anti-transferrin receptor antibody (OX26) through the blood-brain barrier in the rat," Journal of Neurochemistry, 79(1):119-129 (2001).
Moroo, I. et al. "Identification of a Novel Route of iron Transcytosis across the Mammalian Blood-Brain Barrier," Microcirculation, 10(6):457-462 (2003).
Muraszoko, K. et al., "Pharmacokinetics and toxicology of immunotoxins administered into the subarachnoid space in nonhuman primates and rodents," Cancer Research, 53(16):3752-3757 (1993).
Muruganandam, A. et al., "Selection of phage-displayed llama single-domain antibodies that transmigrate across human blood-brain barrier endothelium," FASEB Journal, 16(2):240-242 (2001).
Pardridge, W. M. et al., "Transport of human recombinant brain-derived neurotrophic factor (BDNF) through the rat blood-brain barrier in vivo using vector-mediated peptide drug delivery," Pharmaceutical Research, 11(50:738-746 (1994).
Pardridge, W. M. et al., "Vector-mediated delivery of a polyamide ("peptide") nucleic acid analogue through the blood-brain barrier in vivo," Proc. Natl. Acad. Sci. USA, 92(12):5592-5596 (1995).

Parenti, G., "Treating lysosomal storage diseases with pharmacological chaperones: from concept to clinics," EMBO Mol. Med., 1:268-279 (2009).
Qian, Z. M. et al., "Targeted drug delivery via the transferrin receptor-mediated endocytosis pathway," Pharmacol. Rev., 54(4):561-587 (2002).
Queen, C. et al., "A humanized antibody that binds to the interleukin 2 receptor," Proc. Natl. Acad. Sci. USA, 86:10029-10033 (1988).
Richardson, D. R. et al., "The uptake of iron and transferrin by the human malignant melanoma cell," Biochimica et Biophysica Acta, 1053:1-12 (1990).
Robinson, L. J. et al., "NSF is required for transport from early to late endosomes," Journal of Cell Science, 110:2079-2087 (1997).
Rose, T. M. et al., "Primary Structure of the Human Melanoma-Associated Antigen P97 (Melanotransferrin) Deduced from the MRNA Sequence," Proc. Natl. Acad. Sci. USA, 83:1261-1265 (1986).
Saito, Y. et al., "Vector-mediated delivery of $^{125}$1-labeled beta-amyloid peptide Aβ1-40 through the blood-brain barrier and binding to Alzheimer's disease amytoid of the Aβ1-40/vector complex," Proc. Natl. Acad. Sci. USA, 92(22):10227-10231 (1995).
Sala, R. et al., "The Human Melanoma Associated Protein Melanotransferrin Promotes Endothelial Cell Migration and Angiogenesis in vivo," European Journal of Cell Biology, 81(11):599-607 (2002).
Sato, K. et al., "Reshaping a human antibody to inhibit the interleukin 6-dependent tumor cell growth," Cancer Res., 53:851-856 (1993).
Shi, N. et al., "Noninvasive gene targeting to the brain," Proc. Natl. Acad. Sci. USA, 97(13):7567-7572 (2000).
Skarlatos, S. et al., "Transport of [125]transferrin through the rat blood-brain barrier," Brain Research, 683(2):164-171 (1995).
Song, B. W. et al., "Enhanced neuroprotective effects of basic fibroblast growth factor in regional brain ischemia after conjugation to a blood-brain barrier delivery vector," Journal of Pharmacology and Experimental Therapeutics, 301(2):605-610 (2002).
Srinivasachar, K. et al., "New protein cross-linking reagents that are cleaved by mild acid," Biochem. 28:2501-2509 (1989).
Stefano, J. E. et al., "In vitro and in vivo evaluation of a non-carbohydrate targeting platform for lysosomal proteins," Journal of Controlled Release, 135:113-118 (2009).
Tang, Y. et al., "Directing adenovirus across the blood-brain barrier via melanotransferrin (P97) transcytosis pathway in an vitro model," Gene Therapy, 14(6):523-532 (2007).
WikiPedia Foundation, Inc., Sandhoff disease, http://en.wikipedia.org/wiki/Sandhof_disease, Modified 2007 (Printed Jan. 16, 2008).
Wu, D. et al., "Pharmacokinetics and brain uptake of biotinylated basic fibroblast growth factor conjugated to a blood-brain barrier drug delivery system," Journal of Drug Targeting, 10(3):239-245 (2002).
Wu, D. et al., "Central nervous system pharmacologic effect in conscious rate after intravenous injection of a biotinylated vasoactive intestinal peptide analog coupled to a blood-brain barrier drug delivery system," Journal of Pharmacology and Experimental Therapeutics, 279(1):77-83 (1996).
Wu, D. et al., "Pharmacokinetics and blood-brain transport of [3H]-biotinylated phosphorothioate oligodeoxynucleotide conjugated to a vector-mediated drug delivery system," Journal of Pharmacology and Experimental Therapeutics, 276(1):206-211 (1996).
Yang, J. et al., "Deletion of the GPI pre-anchor sequence in human p97—a general approach for generating the soluble form of GPI-linked proteins," Protein Expression and Purification, 34(1):28-48 (2004).
Yoshikawa, T. et al., "Biotin delivery to brain with a covalent conjugate of avidin and a monoclonal antibody to the transferrin receptor," Journal of Pharmacology and Experimental Therapeutics, 263(2):897-903 (1992).
Zhang, Y. et al., "Conjugation of brain-derived neurotrophic factor to a blood-brain barrier drug targeting system enables neuroprotection in regional brain ischemia following intravenous injection of the neurotrophin," Brain Research, 889(1-2):49-56 (2001).

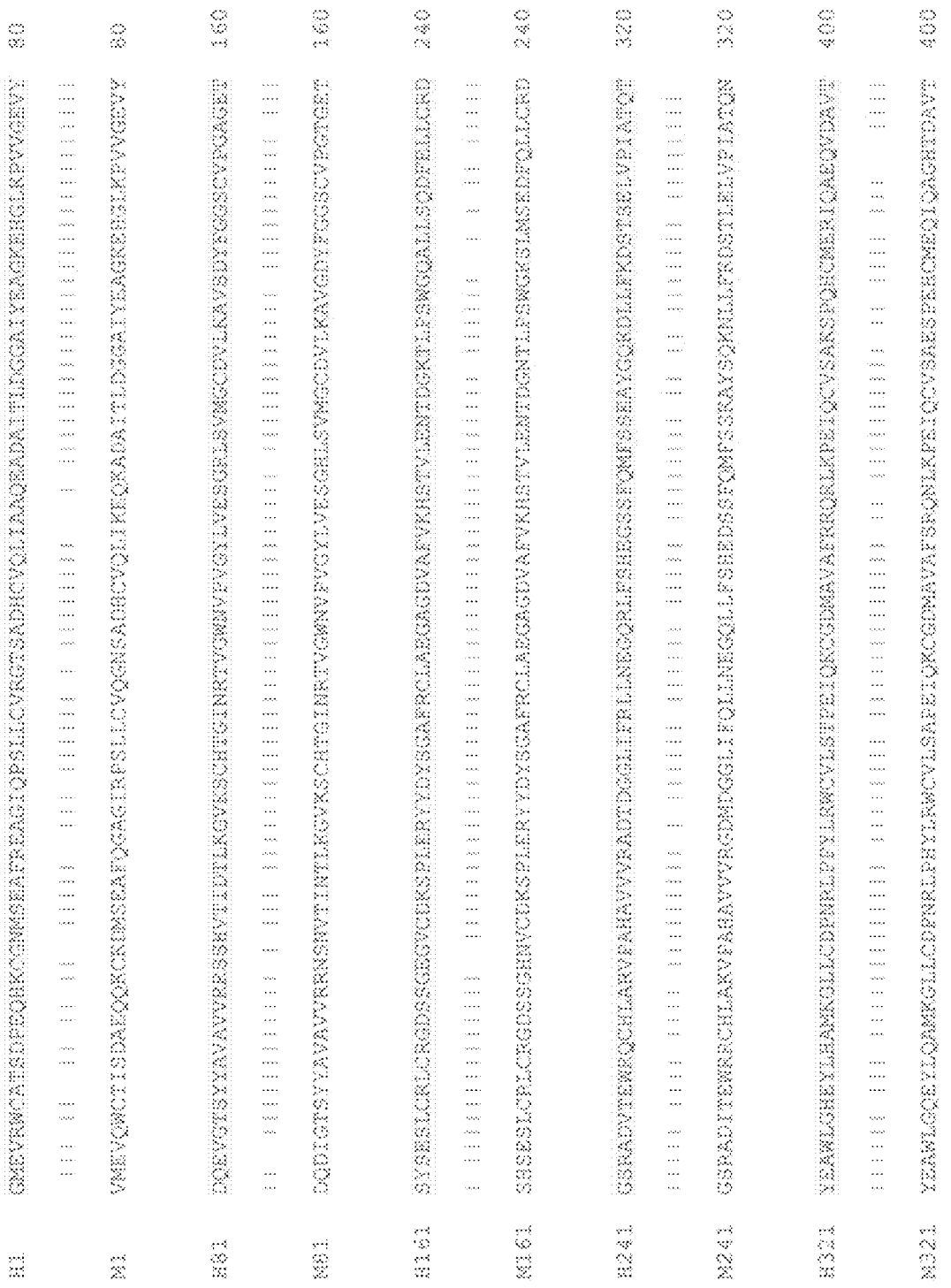

FIG. 1 (Continued)

```
                      SEQUENCE LISTING

<160> NUMBER OF SEQ ID NOS: 13

<210> SEQ ID NO 1
<211> LENGTH: 564
<212> TYPE: PRT
<213> ORGANISM: Homo sapiens

<400> SEQUENCE: 1

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
```

-continued

```
            225                 230                 235                 240
        Gly Ser Arg Ala Asp Val Thr Glu Trp Arg Gln Cys His Leu Ala Arg
                        245                 250                 255
        Val Pro Ala His Ala Val Val Arg Ala Asp Thr Asp Gly Gly Leu
                        260                 265                 270
        Ile Phe Arg Leu Leu Asn Glu Gly Gln Arg Leu Phe Ser His Glu Gly
                        275                 280                 285
        Ser Ser Phe Gln Met Phe Ser Ser Glu Ala Tyr Gly Gln Lys Asp Leu
                        290                 295                 300
        Leu Phe Lys Asp Ser Thr Ser Glu Leu Val Pro Ile Ala Thr Gln Thr
        305                 310                 315                 320
        Tyr Glu Ala Trp Leu Gly His Glu Tyr Leu His Ala Met Lys Gly Leu
                        325                 330                 335
        Leu Cys Asp Pro Asn Arg Leu Pro Pro Tyr Leu Arg Trp Cys Val Leu
                        340                 345                 350
        Ser Thr Pro Glu Ile Gln Lys Cys Gly Asp Met Ala Val Ala Phe Arg
                        355                 360                 365
        Arg Gln Arg Leu Lys Pro Glu Ile Gln Cys Val Ser Ala Lys Ser Pro
        370                 375                 380
        Gln His Cys Met Glu Arg Ile Gln Ala Glu Gln Val Asp Ala Val Thr
        385                 390                 395                 400
        Leu Ser Gly Glu Asp Ile Tyr Thr Ala Gly Lys Lys Tyr Gly Leu Val
                        405                 410                 415
        Pro Ala Ala Gly Glu His Tyr Ala Pro Glu Asp Ser Ser Asn Ser Tyr
                        420                 425                 430
        Tyr Val Val Ala Val Val Arg Arg Asp Ser Ser His Ala Phe Thr Leu
                        435                 440                 445
        Asp Glu Leu Arg Gly Lys Arg Ser Cys His Ala Gly Phe Gly Ser Pro
                        450                 455                 460
        Ala Gly Trp Asp Val Pro Val Gly Ala Leu Ile Gln Arg Gly Phe Ile
        465                 470                 475                 480
        Arg Pro Lys Asp Cys Asp Val Leu Thr Ala Val Ser Glu Phe Phe Asn
                        485                 490                 495
        Ala Ser Cys Val Pro Val Asn Asn Pro Lys Asn Tyr Pro Ser Ser Leu
                        500                 505                 510
        Cys Ala Leu Cys Val Gly Asp Glu Gln Gly Arg Asn Lys Cys Val Gly
                        515                 520                 525
        Asn Ser Gln Glu Arg Tyr Tyr Gly Tyr Arg Gly Ala Phe Arg Cys Leu
                        530                 535                 540
        Val Glu Asn Ala Gly Asp Val Ala Phe Val Arg His Thr Thr Val Phe
        545                 550                 555                 560
        Asp Asn Thr Asn

<210> SEQ ID NO 2
<211> LENGTH: 22
<212> TYPE: PRT
<213> ORGANISM: Homo sapiens

<400> SEQUENCE: 2

Gly His Asn Ser Glu Pro Trp Ala Ala Glu Leu Arg Ser Glu Asp Tyr
        1               5                   10                  15
        Glu Leu Leu Cys Pro Asn
                        20
```

```
<210> SEQ ID NO 3
<211> LENGTH: 51
<212> TYPE: PRT
<213> ORGANISM: Homo sapiens

<400> SEQUENCE: 3

Gly Ala Arg Ala Glu Val Ser Gln Phe Ala Ala Cys Asn Leu Ala Gln
1               5                   10                  15

Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp Asp His
        35                  40                  45

Asn Lys Asn
    50

<210> SEQ ID NO 4
<211> LENGTH: 53
<212> TYPE: PRT
<213> ORGANISM: Homo sapiens

<400> SEQUENCE: 4

Gly Phe Lys Met Phe Asp Ser Ser Asn Tyr His Gly Gln Asp Leu Leu
1               5                   10                  15

Phe Lys Asp Ala Thr Val Arg Ala Val Pro Val Gly Glu Lys Thr Thr
            20                  25                  30

Tyr Arg Gly Trp Leu Gly Leu Asp Tyr Val Ala Ala Leu Glu Gly Met
        35                  40                  45

Ser Ser Gln Gln Cys
    50

<210> SEQ ID NO 5
<211> LENGTH: 586
<212> TYPE: PRT
<213> ORGANISM: Homo sapiens

<400> SEQUENCE: 5

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175
```

```
Glu Gly Val Cys Asp Lys Ser Pro Leu Glu Arg Tyr Asp Tyr Ser
            180                 185                 190
Gly Ala Phe Arg Cys Leu Ala Glu Gly Ala Gly Asp Val Ala Phe Val
        195                 200                 205
Lys His Ser Thr Val Leu Glu Asn Thr Asp Gly Lys Thr Leu Pro Ser
    210                 215                 220
Trp Gly Gln Ala Leu Leu Ser Gln Asp Phe Glu Leu Leu Cys Arg Asp
225                 230                 235                 240
Gly Ser Arg Ala Asp Val Thr Glu Trp Arg Gln Cys His Leu Ala Arg
                245                 250                 255
Val Pro Ala His Ala Val Val Arg Ala Asp Thr Asp Gly Gly Leu
            260                 265                 270
Ile Phe Arg Leu Leu Asn Glu Gly Gln Arg Leu Phe Ser His Glu Gly
        275                 280                 285
Ser Ser Phe Gln Met Phe Ser Ser Glu Ala Tyr Gly Gln Lys Asp Leu
    290                 295                 300
Leu Phe Lys Asp Ser Thr Ser Glu Leu Val Pro Ile Ala Thr Gln Thr
305                 310                 315                 320
Tyr Glu Ala Trp Leu Gly His Glu Tyr Leu His Ala Met Lys Gly Leu
                325                 330                 335
Leu Cys Asp Pro Asn Arg Leu Pro Pro Tyr Leu Arg Trp Cys Val Leu
            340                 345                 350
Ser Thr Pro Glu Ile Gln Lys Cys Gly Asp Met Ala Val Ala Phe Arg
        355                 360                 365
Arg Gln Arg Leu Lys Pro Glu Ile Gln Cys Val Ser Ala Lys Ser Pro
    370                 375                 380
Gln His Cys Met Glu Arg Ile Gln Ala Glu Gln Val Asp Ala Val Thr
385                 390                 395                 400
Leu Ser Gly Glu Asp Ile Tyr Thr Ala Gly Lys Lys Tyr Gly Leu Val
                405                 410                 415
Pro Ala Ala Gly Glu His Tyr Ala Pro Glu Asp Ser Ser Asn Ser Tyr
            420                 425                 430
Tyr Val Val Ala Val Val Arg Arg Asp Ser Ser His Ala Phe Thr Leu
        435                 440                 445
Asp Glu Leu Arg Gly Lys Arg Ser Cys His Ala Gly Phe Gly Ser Pro
    450                 455                 460
Ala Gly Trp Asp Val Pro Val Gly Ala Leu Ile Gln Arg Gly Phe Ile
465                 470                 475                 480
Arg Pro Lys Asp Cys Asp Val Leu Thr Ala Val Ser Glu Phe Phe Asn
                485                 490                 495
Ala Ser Cys Val Pro Val Asn Asn Pro Lys Asn Tyr Pro Ser Ser Leu
            500                 505                 510
Cys Ala Leu Cys Val Gly Asp Glu Gln Gly Arg Asn Lys Cys Val Gly
        515                 520                 525
Asn Ser Gln Glu Arg Tyr Tyr Gly Tyr Arg Gly Ala Phe Arg Cys Leu
    530                 535                 540
Val Glu Asn Ala Gly Asp Val Ala Phe Val Arg His Thr Thr Val Phe
545                 550                 555                 560
Asp Asn Thr Asn Gly His Asn Ser Glu Pro Trp Ala Ala Glu Leu Arg
                565                 570                 575
Ser Glu Asp Tyr Glu Leu Leu Cys Pro Asn
            580                 585
```

<210> SEQ ID NO 6
<211> LENGTH: 637
<212> TYPE: PRT
<213> ORGANISM: Homo sapiens

<400> SEQUENCE: 6

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365

Arg Gln Arg Leu Lys Pro Glu Ile Gln Cys Val Ser Ala Lys Ser Pro
    370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Lys Tyr Gly Leu Val
            405                 410                 415

Pro Ala Ala Gly Glu His Tyr Ala Pro Glu Asp Ser Ser Asn Ser Tyr
        420                 425                 430

Tyr Val Ala Val Val Arg Arg Asp Ser Ser His Ala Phe Thr Leu
    435                 440                 445

Asp Glu Leu Arg Gly Lys Arg Ser Cys His Ala Gly Phe Gly Ser Pro
450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
    530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
        595                 600                 605

Met Val Arg Pro Asp Thr Asn Ile Phe Thr Val Tyr Gly Leu Leu Asp
    610                 615                 620

Lys Ala Gln Asp Leu Phe Gly Asp Asp His Asn Lys Asn
625                 630                 635

<210> SEQ ID NO 7
<211> LENGTH: 73
<212> TYPE: PRT
<213> ORGANISM: Homo sapiens

<400> SEQUENCE: 7

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
            20                  25                  30

Ala Cys Asn Leu Ala Gln Ile Pro Pro His Ala Val Met Val Arg Pro
        35                  40                  45

Asp Thr Asn Ile Phe Thr Val Tyr Gly Leu Leu Asp Lys Ala Gln Asp
    50                  55                  60

Leu Phe Gly Asp Asp His Asn Lys Asn
65                  70

<210> SEQ ID NO 8
<211> LENGTH: 126
<212> TYPE: PRT
<213> ORGANISM: Homo sapiens

<400> SEQUENCE: 8

-continued

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
            20                  25                  30

Ala Cys Asn Leu Ala Gln Ile Pro Pro His Ala Val Met Val Arg Pro
        35                  40                  45

Asp Thr Asn Ile Phe Thr Val Tyr Gly Leu Leu Asp Lys Ala Gln Asp
    50                  55                  60

Leu Phe Gly Asp Asp His Asn Lys Asn Gly Phe Lys Met Phe Asp Ser
65                  70                  75                  80

Ser Asn Tyr His Gly Gln Asp Leu Leu Phe Lys Asp Ala Thr Val Arg
                85                  90                  95

Ala Val Pro Val Gly Glu Lys Thr Thr Tyr Arg Gly Trp Leu Gly Leu
            100                 105                 110

Asp Tyr Val Ala Ala Leu Glu Gly Met Ser Ser Gln Gln Cys
        115                 120                 125

<210> SEQ ID NO 9
<211> LENGTH: 104
<212> TYPE: PRT
<213> ORGANISM: Homo sapiens

<400> SEQUENCE: 9

Gly Ala Arg Ala Glu Val Ser Gln Phe Ala Ala Cys Asn Leu Ala Gln
1               5                   10                  15

Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp Asp His
        35                  40                  45

Asn Lys Asn Gly Phe Lys Met Phe Asp Ser Ser Asn Tyr His Gly Gln
    50                  55                  60

Asp Leu Leu Phe Lys Asp Ala Thr Val Arg Ala Val Pro Val Gly Glu
65                  70                  75                  80

Lys Thr Thr Tyr Arg Gly Trp Leu Gly Leu Asp Tyr Val Ala Ala Leu
                85                  90                  95

Glu Gly Met Ser Ser Gln Gln Cys
            100

<210> SEQ ID NO 10
<211> LENGTH: 14
<212> TYPE: DNA
<213> ORGANISM: Homo sapiens
<220> FEATURE:
<221> NAME/KEY: misc_feature
<222> LOCATION: (1)..(14)
<223> OTHER INFORMATION: Primer

<400> SEQUENCE: 10
gcggacttcc tcgg                                                         14

<210> SEQ ID NO 11
<211> LENGTH: 13
<212> TYPE: DNA
<213> ORGANISM: Homo sapiens
<220> FEATURE:
<221> NAME/KEY: misc_feature
<222> LOCATION: (1)..(13)
<223> OTHER INFORMATION: Primer

<400> SEQUENCE: 11
tcgcgagctt cct                                                                                      13

<210> SEQ ID NO 12
<211> LENGTH: 690
<212> TYPE: PRT
<213> ORGANISM: Homo sapiens

<400> SEQUENCE: 12

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365

```
Arg Gln Arg Leu Lys Pro Glu Ile Gln Cys Val Ser Ala Lys Ser Pro
    370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Lys Tyr Gly Leu Val
                405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
            435                 440                 445

Asp Glu Leu Arg Gly Lys Arg Ser Cys His Ala Gly Phe Gly Ser Pro
450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
            595                 600                 605

Met Val Arg Pro Asp Thr Asn Ile Phe Thr Val Tyr Gly Leu Leu Asp
610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
                645                 650                 655

Ala Thr Val Arg Ala Val Pro Val Gly Glu Lys Thr Thr Tyr Arg Gly
            660                 665                 670

Trp Leu Gly Leu Asp Tyr Val Ala Leu Glu Gly Met Ser Ser Gln
            675                 680                 685

Gln Cys
    690

<210> SEQ ID NO 13
<211> LENGTH: 690
<212> TYPE: PRT
<213> ORGANISM: Mus musculus

<400> SEQUENCE: 13

Val Met Glu Val Gln Trp Cys Thr Ile Ser Asp Ala Glu Gln Gln Lys
1               5                   10                  15

Cys Lys Asp Met Ser Glu Ala Phe Gln Gly Ala Gly Ile Arg Pro Ser
                20                  25                  30

Leu Leu Cys Val Gln Gly Asn Ser Ala Asp His Cys Val Gln Leu Ile
```

```
                 35                  40                  45
Lys Glu Gln Lys Ala Asp Ala Ile Thr Leu Asp Gly Ala Ile Tyr
 50                  55                  60

Glu Ala Gly Lys Glu His Gly Leu Lys Pro Val Val Gly Glu Val Tyr
 65                  70                  75                  80

Asp Gln Asp Ile Gly Thr Ser Tyr Tyr Ala Val Ala Val Arg Arg
                     85                  90                  95

Asn Ser Asn Val Thr Ile Asn Thr Leu Lys Gly Val Lys Ser Cys His
                    100                 105                 110

Thr Gly Ile Asn Arg Thr Val Gly Trp Asn Val Pro Val Gly Tyr Leu
                    115                 120                 125

Val Glu Ser Gly His Leu Ser Val Met Gly Cys Asp Val Leu Lys Ala
                    130                 135                 140

Val Gly Asp Tyr Phe Gly Gly Ser Cys Val Pro Gly Thr Gly Glu Thr
145                 150                 155                 160

Ser His Ser Glu Ser Leu Cys Arg Leu Cys Arg Gly Asp Ser Ser Gly
                    165                 170                 175

His Asn Val Cys Asp Lys Ser Pro Leu Glu Arg Tyr Tyr Asp Tyr Ser
                    180                 185                 190

Gly Ala Phe Arg Cys Leu Ala Glu Gly Ala Gly Asp Val Ala Phe Val
                    195                 200                 205

Lys His Ser Thr Val Leu Glu Asn Thr Asp Gly Asn Thr Leu Pro Ser
                    210                 215                 220

Trp Gly Lys Ser Leu Met Ser Glu Asp Phe Gln Leu Leu Cys Arg Asp
225                 230                 235                 240

Gly Ser Arg Ala Asp Ile Thr Glu Trp Arg Arg Cys His Leu Ala Lys
                    245                 250                 255

Val Pro Ala His Ala Val Val Val Arg Gly Asp Met Asp Gly Gly Leu
                    260                 265                 270

Ile Phe Gln Leu Leu Asn Glu Gly Gln Leu Leu Phe Ser His Glu Asp
                    275                 280                 285

Ser Ser Phe Gln Met Phe Ser Ser Lys Ala Tyr Ser Gln Lys Asn Leu
                    290                 295                 300

Leu Phe Lys Asp Ser Thr Leu Glu Leu Val Pro Ile Ala Thr Gln Asn
305                 310                 315                 320

Tyr Glu Ala Trp Leu Gly Gln Gly Tyr Leu Gln Ala Met Lys Gly Leu
                    325                 330                 335

Leu Cys Asp Pro Asn Arg Leu Pro His Tyr Leu Arg Trp Cys Val Leu
                    340                 345                 350

Ser Ala Pro Glu Ile Gln Lys Cys Gly Asp Met Ala Val Ala Phe Ser
                    355                 360                 365

Arg Gln Asn Leu Lys Pro Glu Ile Gln Cys Val Ser Ala Glu Ser Pro
                    370                 375                 380

Glu His Cys Met Glu Gln Ile Gln Ala Gly His Thr Asp Ala Val Thr
385                 390                 395                 400

Leu Arg Gly Glu Asp Ile Tyr Arg Ala Gly Lys Val Tyr Gly Leu Val
                    405                 410                 415

Pro Ala Ala Gly Glu Leu Tyr Ala Glu Glu Asp Arg Ser Asn Ser Tyr
                    420                 425                 430

Phe Val Val Ala Val Ala Arg Arg Asp Ser Ser Tyr Ser Phe Thr Leu
                    435                 440                 445

Asp Glu Leu Arg Gly Lys Arg Ser Cys His Pro Tyr Leu Gly Ser Pro
450                 455                 460
```

-continued

```
Ala Gly Trp Glu Val Pro Ile Gly Ser Leu Ile Gln Arg Gly Phe Ile
465                 470                 475                 480

Arg Pro Lys Asp Cys Asp Val Leu Thr Ala Val Ser Gln Phe Phe Asn
            485                 490                 495

Ala Ser Cys Val Pro Val Asn Asn Pro Lys Asn Tyr Pro Ser Ala Leu
            500                 505                 510

Cys Ala Leu Cys Val Gly Asp Glu Lys Gly Arg Asn Lys Cys Val Gly
        515                 520                 525

Ser Ser Gln Glu Arg Tyr Tyr Gly Tyr Ser Gly Ala Phe Arg Cys Leu
        530                 535                 540

Val Glu His Ala Gly Asp Val Ala Phe Val Lys His Thr Thr Val Phe
545                 550                 555                 560

Glu Asn Thr Asn Gly His Asn Pro Glu Pro Trp Ala Ser His Leu Arg
                565                 570                 575

Trp Gln Asp Tyr Glu Leu Leu Cys Pro Asn Gly Ala Arg Ala Glu Val
            580                 585                 590

Asp Gln Phe Gln Ala Cys Asn Leu Ala Gln Met Pro Ser His Ala Val
        595                 600                 605

Met Val Arg Pro Asp Thr Asn Ile Phe Thr Val Tyr Gly Leu Leu Asp
        610                 615                 620

Lys Ala Gln Asp Leu Phe Gly Asp Asp His Asn Lys Asn Gly Phe Gln
625                 630                 635                 640

Met Phe Asp Ser Ser Lys Tyr His Ser Gln Asp Leu Leu Phe Lys Asp
                645                 650                 655

Ala Thr Val Arg Ala Val Pro Val Arg Glu Lys Thr Thr Tyr Leu Asp
            660                 665                 670

Trp Leu Gly Pro Asp Tyr Val Val Ala Leu Glu Gly Met Leu Ser Gln
        675                 680                 685

Gln Cys
    690
```

P97 FRAGMENTS WITH TRANSFER ACTIVITY

CROSS-REFERENCE TO RELATED APPLICATIONS

This application is a Continuation of U.S. application Ser. No. 13/566,260, filed Aug. 3, 2012, which claims benefit under 35 U.S.C. §119(e) of U.S. Provisional Application No. 61/515,792, filed Aug. 5, 2011, each of which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is BIOA_004_02US_ST25.txt. The text file is about 32 KB, was created on Mar. 26, 2014, and is being submitted electronically via EFS-Web.

BACKGROUND

1. Technical Field

The present invention is related to fragments of human melanotransferrin (p97). In particular, this invention relates to treatment of diseases through the introduction of the melanotransferrin fragment conjugated to a therapeutic or diagnostic agent to a subject.

2. Description of the Related Art

Melanotransferrin (MTf) is a bi-lobed protein belonging to the transferrin (Tf) family of iron binding proteins. It has been demonstrated previously that MTf is able to directly bind and transport iron into mammalian cells independent of Tf and Tf receptor (TfR). Unlike other Tf family members, this molecule exists in two forms in humans, a glycosyl-phosphatidylinositol (GPI)-linked cell surface form and a secreted water-soluble form. Additionally, MTf is also found to be expressed on human brain endothelium where it is hypothesized to transport iron across the blood brain barrier (BBB). The role of MTf in the transfer of iron into the brain was assessed by following both radiolabeled soluble MTf and Tf into the mouse brain during a 24-hour period (Moroo et al., 2003, Demeule et al., 2002). It was determined that soluble MTf does have the ability to transcytose across the blood-brain barrier (BBB) and this transport was more efficient than that of Tf.

Subsequently, it has been demonstrated that soluble MTf could be used as a delivery vehicle of therapeutics into the brain (Karkan et al., 2008). Pharmacokinetics studies on soluble MTf demonstrated that the clearance of MTf from serum was much greater than IgG control, and was rapidly distributed to the tissues relative to IgG control. The transport of soluble MTf into the brain as a percentage of injected dose was significantly greater than IgG during the first hour post injection. The accumulation of soluble MTf in the brain was found to be significantly more than that of IgG during the first 6-hours post injection.

Furthermore, it was shown that soluble MTf is able to deliver iron across the BBB (Moroo et al., 2003), as well as paclitaxel covalently linked to MTf (Karkan et al., 2008). In the same study, while both free-adriamycin and MTf-adriamycin conjugates were able to equally inhibit the subcutaneous growth of gliomas outside of the brain, only MTf-adriamycin conjugates significantly prolonged the survival of animals bearing intracranial gliomas when compared to the free-adriamycin control (Karkan et al., 2008). Taken together, these data suggest soluble MTf as a potential drug delivery tool.

However, an even more efficient transfer molecule for delivering a target agent would be useful for therapeutic and diagnostic purposes. The present invention addresses these and other needs.

BRIEF SUMMARY

Embodiments of the present invention include isolated p97 (melanotransferrin; MTf) polypeptides consisting of the amino acid sequence set forth in SEQ ID NO:1-8 or 9. Also included are compositions comprising a fragment of p97 consisting essentially of SEQ ID NO:1-8 or 9 and a therapeutic or diagnostic agent.

In some embodiments, the p97 polypeptide is labeled with a label selected from the group consisting of fluorescent molecules, luminescent molecules, enzymes, substances having therapeutic activity, toxins, and radionuclides. In certain embodiments, the p97 polypeptide is conjugated to a therapeutic agent or drug.

Particular embodiments include pharmaceutical compositions comprising a therapeutically effective amount of compound comprising a p97 fragment covalently linked to a therapeutic agent and a pharmaceutically acceptable excipient, wherein the p97 fragment consists of the amino acid sequence set forth in SEQ ID NO:1-8 or 9.

Also included are compositions for delivering an agent across the blood brain barrier comprising a p97 fragment conjugated to the agent, a substance which is capable of specifically binding to p97 conjugated to the agent, or a p97 fragment fusion protein containing the p97 fragment fused to the agent, and a pharmaceutically acceptable carrier or diluent, wherein the p97 fragment consists of the amino acid sequence set forth in SEQ ID NO:1-8 or 9.

Also included are conjugates, comprising a p97 polypeptide that consists or consists essentially of SEQ ID NO:1-8 or 9, where the p97 polypeptide is covalently or operatively linked to an agent, to form a p97-agent conjugate. In some embodiments, the agent is a small molecule, a polypeptide, or a label (i.e., a detectable entity).

In particular embodiments, the small molecule is a cytotoxic or chemotherapeutic or anti-angiogenic agent selected from one or more of alkylating agents, anti-metabolites, anthracyclines, anti-tumor antibiotics, platinums, type I topoisomerase inhibitors, type II topoisomerase inhibitors, vinca alkaloids, and taxanes. In specific embodiments, the small molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof.

In some embodiments, the polypeptide is an antibody or antigen-binding fragment thereof. In particular embodiments, the antibody or antigen-binding fragment thereof specifically binds to one or more of human Her2/neu, Her1/EGFR, CD20, VEGF, CD52, CD33, CTLA-4, tenascin, alpha-4 (α4) integrin, IL-23, amyloid-β, Huntingtin, CD25, nerve growth factor (NGF), TrkA, TNF-α, TNF-β, or α-synuclein, among other targets described herein.

In certain embodiments, the antibody is selected from one or more of trastuzumab, cetuximab, daclizumab, tanezumab, 3F8, abagovomab, adalimumab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, certolizumab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etanercept, etaracizumab, farletuzumab, FBTA05, figitumumab, flanvotumab, galiximab, gemtuzumab, ganitumab, gemtuzumab (ozogamicin), girentuximab, glembatumumab (vedotin), golimumab, ibritumomab tiuxetan, icrucumab, igovomab, indatuximab ravtansine, infliximab, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, tucotuzumab (celmoleukin), ublituximab, urelumab, veltuzumab, volociximab, votumumab, and zalutumumab, among other antibodies described herein, and including antigen-binding fragments thereof.

In some embodiments, the polypeptide is an interferon-β polypeptide, or an active fragment or variant thereof.

In further embodiments, the polypeptide associates with a lysosomal storage disease. In some aspects, the polypeptide is selected from one or more of aspartylglucosaminidase, acid lipase, cysteine transporter, Lamp-2, α-galactosidase A, acid ceramidase, α-L-fucosidase, β-hexosaminidase A, GM2-ganglioside activator (GM2A), α-D-mannosidase, β-D-mannosidase, arylsulfatase A, saposin B, neuraminidase, α-N-acetylglucosaminidase phosphotransferase, phosphotransferase γ-subunit, L-iduronidase, iduronate-2-sulfatase, heparan-N-sulfatase, α-N-acetylglucosaminidase, acetylCoA:N-acetyltransferase, N-acetylglucosamine 6-sulfatase, galactose 6-sulfatase, β-galactosidase, N-acetylgalactosamine 4-sulfatase, hyaluronoglucosaminidase, sulfatases, palmitoyl protein thioesterase, tripeptidyl peptidase I, acid sphingomyelinase, cathepsin A, cathepsin K, α-galactosidase B, NPC1, NPC2, sialin, and sialic acid transporter, including active fragments and variants thereof.

In particular embodiments, the detectable entity is selected from one or more of diatrizoic acid, a radioisotope, a fluorophore/fluorescent dye, and a nanoparticle.

In some embodiments, the agent is a cardiotoxic agent in its unconjugated form. Particular examples include where the cardiotoxic agent is an anthracycline/anthraquinolone, cyclophosphamide, antimetabolite, antimicrotubule agent, tyrosine kinase inhibitor, bevacizumab, or trastuzumab. Additional examples include where the cardiotoxic agent is cyclopentenyl cytosine, 5-fluorouracil, capecitabine, paclitaxel, docataxel, adriamycin, doxorubucin, epirubicin, emetine, isotamide, mitomycin C, erlotinib, gefitinib, imatinib, sorafenib, sunitinib, cisplatin, thalidomide, busulfan, vinblastine, bleomycin, vincristine, arsenic trioxide, methotrexate, rosiglitazone, or mitoxantrone.

Some embodiments include compositions (for example, pharmaceutical compositions), comprising a conjugate described herein, and a pharmaceutically acceptable carrier.

Also included are methods of treating a subject in need thereof, comprising administering to the subject a conjugate or composition described herein.

Some methods are for treating a cancer of the central nervous system (CNS), optionally the brain. Particular methods are for treating primary cancer of the CNS, optionally the brain. Specific methods are for treating a metastatic cancer of the CNS, optionally the brain. In some embodiments, the methods are for treating a glioma, meningioma, pituitary adenoma, vestibular schwannoma, primary CNS lymphoma, neuroblastoma, or primitive neuroectodermal tumor (medulloblastoma). In certain aspects, the glioma is an astrocytoma, oligodendroglioma, ependymoma, or a choroid plexus papilloma.

Particular embodiments are for treating glioblastoma multiforme. In specific aspects, the glioblastoma multiforme is a giant cell gliobastoma or a gliosarcoma.

Certain methods are for treating a lysosomal storage disease. Exemplary lysosomal storage diseases include those selected from one or more of aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, Gaucher disease, globoid cell leucodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leucodystrophy, mucolipidosis type I, sialidosis types I/II mucolipidosis types II/III I-cell disease, mucolipidosis type IIIC pseudo-Hurler polydystrophy, mucopolysaccharidosis type I, mucopolysaccharidosis type II (Hunter syndrome), mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease types NB, Niemann-Pick disease, Niemann-Pick disease type C1, Niemann-Pick disease type C2, pycnodysostosis, Schindler disease types I/II, Schindler disease, and sialic acid storage disease.

Certain methods are for treating a degenerative or autoimmune disorder of the central nervous system (CNS). In some embodiments, the degenerative or autoimmune disorder of the CNS is Alzheimer's disease, Huntington's disease, Parkinson's disease, or multiple sclerosis (MS).

In some embodiments, the subject is undergoing therapy with an otherwise cardiotoxic agent. Exemplary cardiotoxic agents include anthracyclines/anthraquinolones, cyclophosphamides, antimetabolites, antimicrotubule agents, tyrosine kinase inhibitors, bevacizumab, and trastuzumab. In some aspects, the cardiotoxic agent is cyclopentenyl cytosine, 5-fluorouracil, capecitabine, paclitaxel, docataxel, adriamycin, doxorubicin, epirubicin, emetine, isotamide, mitomycin C, erlotinib, gefitinib, imatinib, sorafenib, sunitinib, cisplatin, thalidomide, busulfan, vinblastine, bleomycin, vincristine, arsenic trioxide, methotrexate, rosiglitazone, or mitoxantrone.

In some of the methods provided herein, the subject has cancer. In particular embodiments, the cancer is one or more of breast cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, an epithelial tumor, bone cancer, or a hematopoietic cancer.

In some embodiments, administration of the conjugate reduces cardiotoxicity of the agent, relative to an unconjugated form of the agent.

In certain aspects, the methods are for treating pain. In some embodiments, the pain is acute pain, chronic pain, neuropathic pain, and/or central pain. In particular embodiments, the pain is nociceptive pain, optionally visceral, deep somatic, or superficial somatic pain. In some embodiments, the pain is breakthrough pain, and where the subject is taking pain medication, and is optionally a subject with cancer pain. In further embodiments, the pain is incident pain. In certain embodiments, the pain has a central nervous system (CNS) component. In particular embodiments, the pain is osteoarthritis, chronic low back pain, bone cancer pain, or interstitial cystitis. In specific embodiments, the osteoarthritis is osteoarthritis of the knee, or osteoarthritis of the hip.

Also included are methods for imaging an organ or tissue component in a subject, comprising (a) administering to the subject a human p97 polypeptide fragment of SEQ ID NO:1-8 or 9, where the polypeptide is conjugated to a detectable entity, and (b) visualizing the detectable entity in the subject. In some embodiments, the organ or tissue compartment comprises the central nervous system. In particular embodiments, where the organ or tissue compartment comprises the brain. In certain aspects, visualizing the detectable entity comprises one or more of fluoroscopy, projectional radiography, X-ray CT-scanning, positron emission tomography (PET), single photon emission computed tomography (SPECT), or magnetic resonance imaging (MRI).

BRIEF DESCRIPTION OF THE SEVERAL VIEWS OF THE DRAWINGS

FIG. 1 shows the protein sequence alignment of human soluble p97 (H; SEQ ID NO:12) and mouse soluble p97(M; SEQ ID NO:13). The lightly shaded region represents the amino acid sequence of a human soluble p97 fragment (SEQ ID NO:1; or residues 1-564 of SEQ ID NO:12).

DETAILED DESCRIPTION

Figure 2:
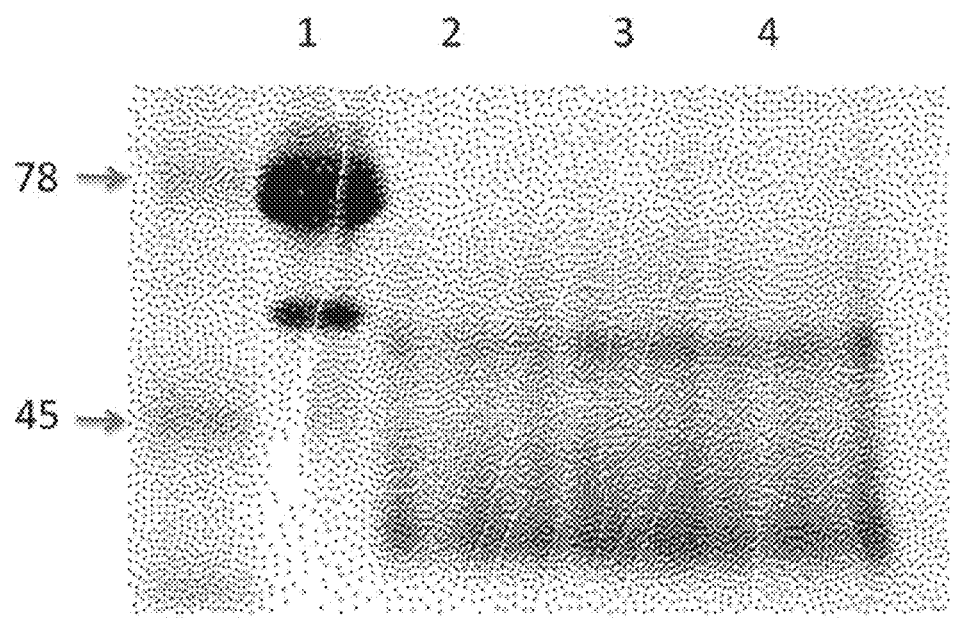
FIG. 2 shows a Coomassie blue stained native PAGE gel. Human p97 was digested over 3 days at 42° C. Lane 1 is human p97, lanes 2 and 3 are human p97 (3 mg) digested with hydroxylamine, and lane 4 is human p97 (5 mg) digested with hydroxylamine.

The present disclosure is based, in pertinent part, on the surprising discovery that a smaller versions of soluble human MTf are able to retain the ability of melanotransferrin (MTf; p97) to cross the blood brain barrier (BBB). In particular, the present invention relates to the fragments of human MTf set forth in SEQ ID NOS:1-9 (see also FIG. 1). Embodiments of the invention pertain to the use of the p97 fragment for the diagnosis, assessment and treatment of diseases and disorders, including, e.g., conditions involving disturbances in iron metabolism, Alzheimer's disease, cancers, and lysosomal storage diseases, among others. In specific embodiments, the invention relates to the p97 fragment conjugated to a therapeutic or diagnostic agent.

As used in this specification and the appended claims, the singular forms "a," "an" and "the" include plural references unless the content clearly dictates otherwise.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements. For certain polypeptide sequences, the phrase "consisting essentially of" can refer to polypeptides of essentially the same length as the recited polypeptide sequence, including those that differ by the addition or deletion of about 1, 2, 3, 4, 5, 6, 7, 8, 9, or 10 N-terminal and/or C-terminal residues.

The term "conjugate" is intended to refer to the entity formed as a result of covalent or non-covalent attachment or linkage of an agent or other molecule, e.g., a biologically active molecule, to a p97 polypeptide. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., *Nucleic Acids Research*. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "linkage," "linker," "linker moiety," or "L" is used herein to refer to a linker that can be used to separate a p97 polypeptide fragment from an agent of interest, or to separate a first agent from another agent, for instance where two or more agents are linked to form a p97 conjugate. The linker may be physiologically stable or may include a releasable linker such as an enzymatically degradable linker (e.g., proteolytically cleavable linkers). In certain aspects, the linker may be a peptide linker, for instance, as part of a p97 fusion protein. In some aspects, the linker may be a non-peptide linker or non-proteinaceous linker. In some aspects, the linker may be particle, such as a nanoparticle.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., the absence of polypeptide of conjugate of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition or a control composition, including all integers in between. As one non-limiting example, a control could compare the activity, such as the amount or rate of transport/delivery across the blood brain barrier, the rate and/or levels of distribution to central nervous system tissue, and/or the $C_{max}$ for plasma, central nervous system tissues, or any other systemic or peripheral non-central nervous system tissues, of a p97-agent conjugate relative to the agent alone. Other examples of comparisons and "statistically significant" amounts are described herein.

In certain embodiments, the "purity" of any given agent (e.g., a p97 polypeptide, a conjugate) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Ha), as the driving force. For purposes herein, a "releasable linker" is synonymous with a "degradable linker." An "enzymatically degradable linkage" includes a linkage, e.g., amino acid sequence, that is subject to degradation by one or more enzymes, e.g., peptidases or proteases. In particular embodiments, a releasable linker has a half life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or less.

The term "reference sequence" refers generally to a nucleic acid coding sequence, or amino acid sequence, to which another sequence is being compared. All polypeptide and polynucleotide sequences described herein are included as references sequences, including those described by name and those described in the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.* 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a p97 polypeptide fragment or conjugate to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, a p97 polypeptide or conjugate has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at about 37° C.

A "subject," as used herein, includes any animal that exhibits a symptom, or is at risk for exhibiting a symptom, which can be treated or diagnosed with a p97 conjugate of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild type gene or gene product (e.g., a polypeptide) is that which is most frequently observed in a population and is thus arbitrarily designed the "normal" or "wild-type" form of the gene.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Compositions and Preparation Thereof

In general, p97 fragment-conjugates may be prepared using techniques well known in the art. There are numerous approaches for the conjugation or chemical crosslinking of agents to a polypeptide such as the p97 fragment, and one skilled in the art can determine which method is most appropriate for conjugating a particular agent. The method employed must be capable of joining the agent with the p97 fragment without interfering with the ability of the p97 fragment to bind to its receptor, preferably without influencing the biodistribution of the p97 fragment-agent compared to the p97 fragment alone, and/or without significantly altering the desired activity of the agent (be it therapeutic or prophylactic or the like) once delivered. A particularly preferred method for linking complex molecules to the p97 fragment is the SATA/sulfo-SMCC cross-linking reaction (Pierce (Rockford, Ill.)).

Methods of cross linking proteins and peptides are well known to those of skill in the art. Several hundred crosslinkers are available for conjugating a compound of interest with the p97 fragment or with a substance which binds the p97 fragment (see, e.g., Chemistry of Protein Conjugation and Crosslinking, Shans Wong, CRC Press, Ann Arbor (1991) and U.S. Pat. No. 5,981,194 and PCT Patent Publication Nos. WO 02/13843 and WO 01/59459 which are incorporated herein by reference in their entirety). Many reagents and cross-linkers can be used to prepare conjugates of an active agent and a p97 fragment molecule. See, for instance, Hermanson, G T et al. Bioconjugate Techniques, Academic Press, (1996). The crosslinker is generally chosen based on the reactive functional groups available or inserted on the therapeutic agent. In addition, if there are no reactive groups, a photoactivatible crosslinker can be used. In certain instances, it may be desirable to include a spacer between the p97 fragment and the agent. In one embodiment, the p97 fragment and the protein therapeutic agents may be conjugated by the introduction of a sulfhydryl group on the p97 fragment and by the introduction of a crosslinker containing a reactive thiol group on to the protein compound through carboxyl groups (Wawizynczak and Thorpe in Immunoconjugates: Antibody Conjugates in Radioimaging and Therapy of Cancer, Vogel (Ed.) Oxford University Press, pp. 28-55 (1987); and Blair and Ghose (1983) J. Immunol. Methods 59:129). In some embodiments, the linker is vulnerable to hydrolysis at the acidic pH of the lysosome so as to free the agent from the p97 fragment and/or linker.

In some embodiments of the present invention, the p97 fragment-agent conjugate is a p97 fragment-fusion protein. Fusion proteins may be prepared using standard techniques known in the art. Typically, a DNA molecule encoding the p97 fragment or a portion thereof is linked to a DNA molecule encoding the protein compound. The chimeric DNA construct, along with suitable regulatory elements can be cloned into an expression vector and expressed in a suitable host. The resultant fusion proteins contain the p97 fragment fused to the selected protein compound.

When a linker is used, the linker is preferably an organic moiety constructed to contain an alkyl, aryl and/or amino acid backbone, and containing an amide, ether, ester, hydrazone, disulphide linkage or any combination thereof. Linkages containing amino acid, ether and amide bound components are stable under conditions of physiological pH, normally 7.4 in serum. Preferred linkages are those containing esters or hydrazones that are stable at serum pH, but that hydrolyze to release the drug when exposed to lysosomal pH. Disulphide linkages are preferred because they are sensitive to reductive cleavage. In addition, amino acid linkers may be designed to be sensitive to cleavage by specific enzymes in the desired target organ or more preferably, the lysosome itself. Exemplary linkers are described in Blattler et al. (19S5) Biochem. 24:1517-1524; King et al (1986) Biochem. 25:5774-5779; Srinivasachar and Nevill (1989) Biochem. 28:2501-2509.

In some embodiments, the linker is a polyethylene glycol or polypropylene glycol. In other embodiments, the linker is from 4 to 20 atoms long. In other embodiments, the linker is from 1 to 30 atoms long with carbon chain atoms which may be substituted by heteroatoms independently selected from the group consisting of 0, N. or S. In some embodiments, from 1-4 or from 5 to 15 of the C atoms are substituted with a heteroatom independently selected from O, N, S. In other embodiments, the linker contains a moiety subject to hydrolysis upon delivery to the lysosomal environment (e.g., susceptible to hydrolysis at the lysosomal pH or upon contact to a lysosomal enzyme). In some embodiments, the linker group is preferably hydrophilic to enhance the solubility of the conjugate in body fluids. In some embodiments, the linker contains or is attached to the p97 fragment molecule or the protein agent by a functional group subject to attack by other lysosomal enzymes (e.g., enzymes not deficient in the target lysosome or a lysosomal enzyme not conjugated to the p97 fragment carrier). In some embodiments, the p97 fragment and agent are joined by a linker comprising amino acids or peptides. lipids, or sugar residues. In some embodiments, the p97 fragment and agent are joined at groups introduced synthetically or by posttranslational modifications.

In some embodiments, agent-linker intermediates are similar to what has been described previously, but comprise, for example, either an active ester that can react with free amine groups on the p97 fragment or a maleimide that can react with the free thiols created on the p97 fragment via a SATA reaction or through other groups where persons skilled in the art can attach them to the p97 fragment.

p97 Sequences.

In some embodiments, a p97 polypeptide comprises, consists essentially of, or consists of at least one of the human p97 fragments identified in SEQ ID NO:1-8 or 9.

In other specific embodiments, a p97 polypeptide sequence comprises a sequence having at least 70%, 75%, 80%, 85%, 90%, 95%, 96%, 97%, 98%, or 99% identity or homology, along its length, to at least one of the human p97 fragments identified in SEQ ID NO:1-8 or 9.

In particular embodiments, the p97 fragment or variant thereof has the ability to cross the BBB, and optionally transport an agent of interest across the BBB and into the central nervous system. In certain embodiments, the p97 fragment or variant thereof is capable of specifically binding to a p97 receptor, an LRP1 receptor, and/or an LRP1B receptor.

Preparation of p97

The p97 fragment for use in the methods and compositions of the present invention may be obtained, isolated or prepared from a variety of sources.

In one aspect, standard recombinant DNA techniques may be used to prepare the p97 fragment. Within one embodiment, DNA encoding the p97 fragment may be obtained by polymerase chain reaction (PCR) amplification of the p97 fragment sequence set forth in SEQ ID NO:1-8 or 9 (see, generally, U.S. Pat. Nos. 4,683,202; 4,683,195; and 4,800,159; see, also, PCR Technology: Principles and Applications for DNA Amplification, Erlich (ed.), Stockton Press (1989)). Briefly, double-stranded DNA from cells which express the p97 fragment (e.g., SK-MEL-28 cells) is denatured by heating in the presence of heat stable Taq polymerase, sequence specific DNA primers such as 5' GCGGACTTCCTCGG 3' (SEQ ID NO:10) and 5' TCGCGAGCTTCCT 3' (SEQ ID NO:11), ATP, CTP, GTP and TTP. Double-stranded DNA is produced when the synthesis is complete. This cycle may be repeated many times, resulting in a factorial amplification of the p97 fragment DNA. The amplified the p97 fragment DNA may then be readily inserted into an expression vector as described below.

Alternatively, DNA encoding the p97 fragment may be isolated using the cloning techniques described by Brown et al. in the UK Patent Application No. GB 2188 637.

As noted above, the present invention provides recombinant expression vectors which include either synthetic, or cDNA-derived DNA fragments encoding the p97 fragment, which are operably linked to suitable transcriptional or translational regulatory elements. Suitable regulatory elements may be derived from a variety of sources, including, but not limited to, bacterial, fungal, viral, mammalian, and insect genes. Selection of appropriate regulatory elements is dependent on the host cell chosen, and may be readily accomplished by one of ordinary skill in the art. Examples of regulatory elements include, in particular, a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, sequences conferring inducible transcription, and selectable markers, may be incorporated into the expression vector.

DNA sequences encoding the p97 fragment may be expressed by a wide variety of prokaryotic and eukaryotic host cells, including, but not limited to, bacterial, mammalian, yeast, fungi, viral, plant, and insect cells. Methods for transforming or transfecting such cells for expressing foreign DNA are well known in the art (see, e.g., Itakura et al, U.S. Pat. No. 4,704,362; Hinnen et al. (1978) PNAS USA 75:1929-1933; Murray et al, U.S. Pat. No. 4,801,542; Upshall et al, U.S. Pat. No. 4,935,349; Hagen et al, U.S. Pat. No. 4,784,950; Axel et al, U.S. Pat. No. 4,399,216; Goeddel et al, U.S. Pat. No. 4,766,075; and Sambrook et al, supra).

Promoters, terminators, and methods for introducing expression vectors of an appropriate type into, for example, plant, avian, and insect cells may be readily accomplished by those of skill in the art. Recombinantly produced p97 fragment may be further purified as described in more detail below.

The soluble form of p97 may be prepared by culturing cells containing the soluble p97 through the log phase of the cell's growth and collecting the supernatant. Preferably, the supernatant is collected prior to the time at which the cells lose viability. Soluble p97 may then be purified as described below, in order to yield isolated soluble p97. Suitable methods for purifying the soluble p97 can be selected based on the hydrophilic property of the soluble p97. For example, the soluble p97 may be readily obtained by Triton X-I 14 Phase Separation. Once the soluble p97 has been purified, it may be digested with, e.g., hydroxylamine as described in the Examples to generate the p97 fragment.

Therapeutic Agents

As noted above, certain embodiments comprise a p97 polypeptide that is linked to a therapeutic agent or drug of interest, for instance, a small molecule or a polypeptide (e.g., peptide, antibody). Also included are conjugates that comprise more than one therapeutic agent of interest, for instance, a p97 fragment conjugated to an antibody and a small molecule.

Covalent linkages are preferred, however, non-covalent linkages can also be employed, including those that utilize relatively strong non-covalent protein-ligand interactions, such as the interaction between biotin and avidin. Operative linkages are also included, which do not necessarily require a directly covalent or non-covalent interaction between the p97 fragment and the agent of interest; examples of such linkages include liposome mixtures that comprise a p97 polypeptide and an agent of interest. Exemplary methods of generating protein conjugates are described herein, and other methods are well-known in the art.

Exemplary small molecules include cytotoxic, chemotherapeutic, and anti-angiogenic agents, for instance, those that have been considered useful in the treatment of various cancers, including cancers of the central nervous system and cancers that have metastasized to the central nervous system. Particular classes of small molecules include, without limitation, alkylating agents, anti-metabolites, anthracyclines, anti-tumor antibiotics, platinums, type I topoisomerase inhibitors, type II topoisomerase inhibitors, vinca alkaloids, and taxanes.

Specific examples of small molecules include chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, and paclitaxel, and pharmaceutically acceptable salts, acids or derivatives of any of the above.

Additional examples of small molecules include those that target protein kinases for the treatment of nervous system (e.g., CNS) disorders, including imatinib, dasatinib, sorafenib, pazopanib, sunitnib, vatalanib, geftinib, erlotinib, AEE-788, dichoroacetate, tamoxifen, fasudil, SB-681323, and semaxanib (SU5416) (see Chico et al., *Nat Rev Drug Discov.* 8:829-909, 2009). Examples of small molecules also include donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, and bexarotene (e.g., for treating Alzheimer's Disease, Parkinson's Disease, Huntington's Disease); and glatirimer acetate, fingolimod, mitoxantrone (e.g., for treating MS). Also included are pharmaceutically acceptable salts, acids or derivatives of any of the above.

Further examples of small molecules include alkylating agents such as thiotepa, cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); especially ramicins; capecitabine; and pharmaceutically acceptable salts, acids or derivatives of any of the above.

Also included are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

As noted above, in certain aspects the small molecule is an otherwise cardiotoxic agent. Particular examples of cardiotoxic small molecules include, without limitation, anthracyclines/anthraquinolones, cyclophosphamides, antimetabolites, antimicrotubule agents, and tyrosine kinase inhibitors. Specific examples of cardiotoxic agents include cyclopentenyl cytosine, 5-fluorouracil, capecitabine, paclitaxel, docataxel, adriamycin, doxorubucin, epirubicin, emetine, isotamide, mitomycin C, erlotinib, gefitinib, imatinib, sorafenib, sunitinib, cisplatin, thalidomide, busulfan, vinblastine, bleomycin, vincristine, arsenic trioxide, methotrexate, rosiglitazone, and mitoxantrone, among other small molecules described herein and known in the art.

In particular embodiments, the therapeutic agent of interest is a peptide or polypeptide. The terms "peptide" and "polypeptide" are used interchangeably herein, however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids, as described herein. Antibodies are also included as polypeptides.

Exemplary polypeptide agents include polypeptides associated with lysosomal storage disorders. Examples of such polypeptides include aspartylglucosaminidase, acid lipase, cysteine transporter, Lamp-2, α-galactosidase A, acid ceramidase, α-L-fucosidase, β-hexosaminidase A, GM2-ganglioside activator (GM2A), α-D-mannosidase, β-D-mannosidase, arylsulfatase A, saposin B, neuraminidase, α-N-acetylglucosaminidase phosphotransferase, phosphotransferase γ-subunit, L-iduronidase, iduronate-2-sulfatase, heparan-N-sulfatase, α-N-acetylglucosaminidase, acetylCoA:N-acetyltransferase, N-acetylglucosamine 6-sulfatase, galactose 6-sulfatase, β-galactosidase, N-acetylgalactosamine 4-sulfatase, hyaluronoglucosaminidase, sulfatases, palmitoyl protein thioesterase, tripeptidyl peptidase I, acid sphingomyelinase, cathepsin A, cathepsin K, α-galactosidase B, NPC1, NPC2, sialin, and sialic acid transporter, including fragments, variants, and derivatives thereof.

Certain embodiments include polypeptides such as interferon-β polypeptides, such as interferon-β1a (e.g., AVONEX, REBIF) and interferon-β1b (e.g., Betaseron), which are often used for the treatment of multiple sclerosis (MS).

In some embodiments, as noted above, the polypeptide agent is an antibody or an antigen-binding fragment thereof. The antibody or antigen-binding fragment used in the conjugates or compositions of the present invention can be of essentially any type. Particular examples include therapeutic and diagnostic antibodies. As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule.

As used herein, the term "antibody" encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

The term "antigen-binding fragment" as used herein refers to a polypeptide fragment that contains at least one CDR of an immunoglobulin heavy and/or light chains that binds to the antigen of interest. In this regard, an antigen-binding fragment of the herein described antibodies may comprise 1, 2, 3, 4, 5, or all 6 CDRs of a VH and VL sequence from antibodies that bind to a therapeutic or diagnostic target.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

A molecule such as an antibody is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Weals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$.

Immunological binding properties of selected antibodies and polypeptides can be quantified using methods well known in the art (see Davies et al., *Annual Rev. Biochem.* 59:439-473, 1990). In some embodiments, an antibody or other polypeptide is said to specifically bind an antigen or epitope thereof when the equilibrium dissociation constant is about ≤$10^{-7}$ or $10^{-8}$ M. In some embodiments, the equilibrium dissociation constant of an antibody may be about ≤$10^{-9}$ M or ≤$10^{-10}$ M. In certain illustrative embodiments, an antibody or other polypeptide has an affinity ($K_d$) for an antigen or target described herein (to which it specifically binds) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the antibody or antigen-binding fragment or other polypeptide specifically binds to a cell surface receptor or other cell surface protein. In some embodiments, the antibody or antigen-binding fragment or other polypeptide specifically binds to a ligand of a cell surface receptor or other cell surface protein. In some embodiments, the antibody or antigen-binding fragment or other polypeptide specifically binds to an intracellular protein.

In certain embodiments, the antibody or antigen-binding fragment thereof or other polypeptide specifically binds to a cancer-associated antigen, or cancer antigen. Exemplary cancer antigens include cell surface proteins such as cell surface receptors. Also included as cancer-associated antigens are ligands that bind to such cell surface proteins or receptors. In specific embodiments, the antibody or antigen-binding fragment specifically binds to a intracellular cancer antigen. In some embodiments, the cancer that associates with the cancer antigen is one or more of breast cancer, metastatic brain cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, epithelial tumor, bone cancer, or a hematopoietic cancer.

In particular embodiments, the antibody or antigen-binding fragment or other polypeptide specifically binds to at least one cancer-associated antigen, or cancer antigen, such as human Her2/neu, Her1/EGF receptor (EGFR), Her3, A33 antigen, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and/or mesothelin.

In specific embodiments, the antibody or antigen-binding fragment thereof or other polypeptide specifically binds to the human Her2/neu protein. Essentially any anti-Her2/neu antibody, antigen-binding fragment or other Her2/neu-specific binding agent may be used in producing the p97-antibody conjugates of the present invention. Illustrative anti-Her2/neu antibodies are described, for example, in U.S. Pat. Nos. 5,677,171; 5,720,937; 5,720,954; 5,725,856; 5,770,195; 5,772,997; 6,165,464; 6,387,371; and 6,399,063, the contents of which are incorporated herein by reference in their entireties.

In some embodiments, the antibody or antigen-binding fragment thereof or other polypeptide specifically binds to the human Her1/EGFR (epidermal growth factor receptor). Essentially any anti-Her1/EGFR antibody, antigen-binding fragment or other Her1-EGFR-specific binding agent may be used in producing the p97-antibody conjugates of the present invention. Illustrative anti-Her1/EGFR antibodies are described, for example, in U.S. Pat. Nos. 5,844,093; 7,132,511; 7,247,301; 7,595,378; 7,723,484; 7,939,072; and 7,960,516, the contents of which are incorporated by reference in their entireties.

In certain embodiments, the antibody is a therapeutic antibody, such as an anti-cancer therapeutic antibody, including antibodies such as 3F8, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, cetuximab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, trastuzumab, tucotuzumab (celmoleukin), ublituximab, urelumab, veltuzumab, volociximab, votumumab, and zalutumumab. Also included are fragments, variants, and derivatives of these antibodies.

In particular embodiments, the antibody is a cardiotoxic antibody, that is, an antibody that displays cardiotoxicity when administered in an unconjugated form. Specific examples of antibodies that display cardiotoxicity include trastuzumab and bevacizumab.

In specific embodiments, the anti-Her2/neu antibody used in a p97 conjugate is trastuzumab (Herceptin®), or a fragment, variant or derivative thereof. Herceptin® is a Her2/neu-specific monoclonal antibody approved for the treatment of human breast cancer. In certain embodiments, a Her2/neu-binding antigen-binding fragment comprises one or more of the CDRs of a Her2/neu antibody. In this regard, it has been shown in some cases that the transfer of only the VHCDR3 of an antibody can be performed while still retaining desired specific binding (Barbas et al., *PNAS*. 92: 2529-2533, 1995). See also, McLane et al., PNAS USA. 92:5214-5218, 1995; and Barbas et al., *J. Am. Chem. Soc.* 116:2161-2162, 1994.

In other specific embodiments, the anti-Her1/EGFR antibody used in a conjugate of the invention is cetuximab (Erbitux®), or a fragment or derivative thereof. In certain embodiments, an anti-Her1/EGFR binding fragment comprises one or more of the CDRs of a Her1/EGFR antibody such as cetuximab. Cetuximab is approved for the treatment of head and neck cancer, and colorectal cancer. Cetuximab is composed of the Fv (variable; antigen-binding) regions of the 225 murine EGFR monoclonal antibody specific for the N-terminal portion of human EGFR with human IgG1 heavy and kappa light chain constant (framework) regions.

In some embodiments, the antibody or antigen-binding fragment or other polypeptide specifically binds to an antigen associated with (e.g., treatment of) at least one nervous system disorder, including disorders of the peripheral and/or central nervous system (CNS) disorder. In certain embodiments, the antibody or antigen-binding fragment or other polypeptide specifically binds to an antigen associated with (e.g., treatment of) pain, including acute pain, chronic pain, and neuropathic pain. In some embodiments, the antibody or antigen-binding fragment or other polypeptide specifically binds an antigen associated with (e.g., treatment of) an autoimmune disorder, including autoimmune disorders of the nervous system or CNS.

Examples of nervous system-, pain-, and/or autoimmune-associated antigens include, without limitation, alpha-4 (α4) integrin, tumor necrosis factor (TNF), IL-12, IL-23, the p40 subunit of IL-12 and IL-23, CD20, CD52, amyloid-β (e.g., $A\beta_{(1-42)}$), Huntingtin, CD25 (i.e., the alpha chain of the IL-2 receptor), nerve growth factor (NGF), neurotrophic tyrosine kinase receptor type 1 (TrkA; the high affinity catalytic receptor for NGF), and α-synuclein. These targets have been considered useful in the treatment of a variety of nervous system, pain, and/or autoimmune disorders, such as multiple sclerosis (α4 integrin, IL-23, CD25, CD20, CD52, IL-12, IL-23, the p40 subunit of IL-12 and IL-23, Nogo-A, LINGO-1), Alzheimer's Disease (Aβ, TNF), Huntington's Disease (Huntingtin), Parkinson's Disease (a-synuclein), and pain (NGF and TrkA).

In specific embodiments, the anti-CD25 antibody used in a p97 conjugate is daclizumab (i.e., Zenapax™), or a fragment, variant or derivative thereof. Daclizumab a humanized monoclonal antibody that specifically binds to CD25, the alpha subunit of the IL-2 receptor. In some embodiments, the antibody is natalizumab, or a variant or fragment thereof that specifically binds to α4 integrin. In other embodiments, the antibody is rituximab, ocrelizumab, ofatumumab, or a variant or fragment thereof that specifically binds to CD20. In particular embodiments, the antibody is alemtuzumab, or a variant or fragment thereof that specifically binds to CD52. In certain embodiments, the antibody is ustekinumab (CNTO 1275), or a variant or fragment thereof that specifically binds to the p40 subunit of IL-12 and IL-23.

In specific embodiments, the anti-NGF antibody used in a conjugate is tanezumab, or a fragment, variant or derivative thereof. Tanezumab specifically binds to NGF and prevents NGF from binding to its high affinity, membrane-bound, catalytic receptor tropomyosin-related kinase A (TrkA), which is present on sympathetic and sensory neurons; reduced stimulation of TrkA by NGF is believed to inhibit the pain-transmission activities of such neurons.

In some embodiments, the antibody used in a conjugate specifically binds to tumor necrosis factor (TNF)-α or TNF-β. In specific embodiments, the anti-TNF antibody is adalimumab (Humira®), certolizumab pegol (Cimzia®), etanercept (Enbrel®), golimumab (Cimzia®), or infliximab (Remicade®), D2E7, CDP 571, or CDP 870, or an antigen-binding fragment or variant thereof. Conjugates comprising an anti-TNF antibody can be used, for instance, in the treatment of neurological conditions or disorders such as Alzheimer's disease, stroke, traumatic brain injury (TBI), spinal stenosis, acute spinal cord injury, spinal cord compression (see U.S. Pat. Nos. 6,015,557; 6,177,077; 6,419,934; 6,419,944; 6,537,549; 6,982,089; and 7,214,658).

Antibodies may be prepared by any of a variety of techniques known to those of ordinary skill in the art. See, e.g., Harlow and Lane, *Antibodies: A Laboratory Manual*, Cold Spring Harbor Laboratory, 1988. Monoclonal antibodies specific for a polypeptide of interest may be prepared, for example, using the technique of Kohler and Milstein, *Eur. J. Immunol.* 6:511-519, 1976, and improvements thereto. Also included are methods that utilize transgenic animals such as mice to express human antibodies. See, e.g., Neuberger et al., *Nature Biotechnology* 14:826, 1996; Lonberg et al., *Handbook of Experimental Pharmacology* 113:49-101, 1994; and Lonberg et al., *Internal Review of Immunology* 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S. Pat. No. 7,244,592; Chao et al., *Nature Protocols*. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art. The p97 polypeptides described herein and known in the art may be used in the purification process in, for example, an affinity chromatography step.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. See Inbar et al., *PNAS USA*. 69:2659-2662, 1972; Hochman et al., *Biochem*. 15:2706-2710, 1976; and Ehrlich et al., *Biochem*. 19:4091-4096, 1980.

In certain embodiments, single chain Fv or scFV antibodies are contemplated. For example, Kappa bodies (III et al., *Prot. Eng.* 10:949-57, 1997); minibodies (Martin et al., *EMBO J* 13:5305-9, 1994); diabodies (Holliger et al., *PNAS* 90: 6444-8, 1993); or Janusins (Traunecker et al., *EMBO J* 10: 3655-59, 1991; and Traunecker et al., *Int. J. Cancer Suppl.* 7:51-52, 1992), may be prepared using standard molecular biology techniques following the teachings of the present application with regard to selecting antibodies having the desired specificity.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (*PNAS USA*. 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an antibody as described herein is in the form of a "diabody." Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). A dAb fragment of an antibody consists of a VH domain (Ward et al., *Nature* 341:544-546, 1989). Diabodies and other multivalent or multispecific fragments can be constructed, for example, by gene fusion (see WO94/13804; and Holliger et al., *PNAS USA*. 90:6444-6448, 1993)).

Minibodies comprising a scFv joined to a CH3 domain are also included (see Hu et al., *Cancer Res*. 56:3055-3061, 1996). See also Ward et al., *Nature*. 341:544-546, 1989; Bird et al., *Science*. 242:423-426, 1988; Huston et al., *PNAS USA*. 85:5879-5883, 1988); PCT/US92/09965; WO94/13804; and Reiter et al., *Nature Biotech*. 14:1239-1245, 1996.

Where bispecific antibodies are to be used, these may be conventional bispecific antibodies, which can be manufactured in a variety of ways (Holliger and Winter, *Current Opinion Biotechnol.* 4:446-449, 1993), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al., *Protein Eng.*, 9:616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US Application No. 2009/0226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies provided herein may take the form of a nanobody. Minibodies are encoded by single genes and are efficiently produced in almost all prokaryotic and eukaryotic hosts, for example, *E. coli* (see U.S. Pat. No. 6,765,087), moulds (for example *Aspergillus* or *Trichoderma*) and yeast (for example *Saccharomyces, Kluyvermyces, Hansenula* or *Pichia* (see U.S. Pat. No. 6,838,254). The production process is scalable and multi-kilogram quantities of nanobodies have been produced. Nanobodies may be formulated as a ready-to-use solution having a long shelf life. The Nanoclone method (see WO 06/079372) is a proprietary method for generating Nanobodies against a desired target, based on automated high-throughput selection of B-cells.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., *PNAS USA* 86:4220-4224, 1989; Queen et al., *PNAS USA*. 86:10029-10033, 1988; Riechmann et al., *Nature*. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., *Cancer Res.* 53:851-856, 1993; Riechmann et al., *Nature* 332:323-327, 1988; Verhoeyen et al., *Science* 239:1534-1536, 1988; Kettleborough et al., *Protein Engineering.* 4:773-3783, 1991; Maeda et al., *Human Antibodies Hybridoma* 2:124-134, 1991; Gorman et al., *PNAS USA.* 88:4181-4185, 1991; Tempest et al., *Bio/Technology* 9:266-271, 1991; Co et al., *PNAS USA.* 88:2869-2873, 1991; Carter et al., *PNAS USA.* 89:4285-4289, 1992; and Co et al., *J Immunol.* 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present invention may be chimeric antibodies. In this regard, a chimeric antibody is comprised of an antigen-binding fragment of an antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

Labels

In some embodiments, the p97 fragment conjugate is labeled to facilitate its detection. A "label" or a "detectable entity" is a composition detectable by spectroscopic, photochemical, biochemical, immunochemical, chemical, or other physical means. For example, labels suitable for use in the present invention include, for example, radioactive labels (e.g., $^{32}$P), fluorophores (e.g., fluorescein), electron-dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the agent, the linker or the p97 fragment portion of a conjugate may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., H, I, S, C, or P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the p97 fragment using an isocyanate reagent for conjugating an active agent according to the invention. In one aspect of the invention, the bifunctional isocyanate reagents of the invention can be used to conjugate a label to the p97 fragment to form a label p97 fragment conjugate without an active agent attached thereto. The label p97 fragment conjugate may be used as an intermediate for the synthesis of a labeled conjugate according to the invention or may be used to detect the p97 fragment conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

Pharmaceutical Compositions, and Methods of Use/Treatment/Administration

Certain embodiments of the present invention relate to methods of using the compositions of p97 polypeptides and p97 conjugates described herein. Examples of such methods include methods of treatment and methods of diagnosis, including for instance, the use of p97 conjugates for medical imaging of certain organs/tissues, such as those of the nervous system. Specific embodiments include methods of diagnosing and/or treating disorders or conditions of the central nervous system (CNS), or disorders or conditions having a CNS component.

Accordingly, certain embodiments include methods of treating a subject in need thereof, comprising administering a composition that comprises a p97 conjugate described herein. Also included are methods of delivering an agent to the nervous system (e.g., central nervous system tissues) of a subject, comprising administering a composition that comprises a p97 conjugate described herein. In certain of these and related embodiments, the methods increase the rate of delivery of the agent to the central nervous system tissues, relative, for example, to delivery by a composition that comprises the agent alone.

In some instances, a subject has a disease, disorder, or condition of the CNS, where increased delivery of a therapeutic agent across the blood brain barrier to CNS tissues relative to peripheral tissues can improve treatment, for instance, by reducing side-effects associated with exposure of an agent to peripheral tissues. Exemplary diseases, disorders, and conditions of the CNS include various cancers, including primary and metastatic CNS cancers, lysosomal storage diseases, neurodegenerative diseases such as Alzheimer's disease, and auto-immune diseases such as multiple sclerosis.

Certain embodiments thus relate to methods for treating a cancer of the central nervous system (CNS), optionally the brain, where the subject in need thereof has such a cancer or is at risk for developing such a condition. In some embodiments, the cancer is a primary cancer of the CNS, such as a primary cancer of the brain. For instance, the methods can be for treating a glioma, meningioma, pituitary adenoma, vestibular schwannoma, primary CNS lymphoma, or primitive neuroectodermal tumor (medulloblastoma). In some embodiments, the glioma is an astrocytoma, oligodendroglioma, ependymoma, or a choroid plexus papilloma. In certain embodiments, the primary CNS or brain cancer is glioblastoma multiforme, such as a giant cell gliobastoma or a gliosarcoma.

In particular embodiments, the cancer is a metastatic cancer of the CNS, for instance, a cancer that has metastasized to the brain. Examples of such cancers include, without limitation, breast cancers, lung cancers, genitourinary tract cancers, gastrointestinal tract cancers (e.g., colorectal cancers, pancreatic carcinomas), osteosarcomas, melanomas, head and neck cancers, prostate cancers (e.g., prostatic adenocarcinomas), and lymphomas. Certain embodiments thus include methods for treating, inhibiting or preventing metastasis of a cancer by administering to a patient a therapeutically effective amount of a herein disclosed conjugate (e.g., in an amount that, following administration, inhibits, prevents or delays metastasis of a cancer in a statistically significant manner, i.e., relative to an appropriate control as will be known to those skilled in the art). In particular embodiments, the subject has a cancer that has not yet metastasized to the central nervous system, including one or more of the above-described cancers, among others known in the art.

In particular embodiments, the cancer (cell) expresses or overexpresses one or more of Her2/neu, CD20, Her1/EGF receptor(s), VEGF receptor(s), PDGF receptor(s), CD30, CD52, CD33, CTLA-4, or tenascin.

Also included is the treatment of other cancers, including breast cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, melanoma, non-melanoma cancer, thyroid cancer, endometrial cancer, epithelial tumor, bone cancer, or a hematopoietic cancer. Hence, in certain embodiments, the cancer cell being treated by a p97 conjugate overexpresses or is associated with a cancer antigen, such as human Her2/neu, Her1/EGF receptor (EGFR), Her3, A33 antigen, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and/or mesothelin.

The use of p97 conjugates for treating cancers including cancers of the CNS can be combined with other therapeutic modalities. For example, a composition comprising a p97 conjugate can be administered to a subject before, during, or after other therapeutic interventions, including symptomatic care, radiotherapy, surgery, transplantation, immunotherapy, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

In specific combination therapies, the antibody portion of an p97-antibody conjugate comprises cetuximab, and the p97-cetuximab conjugate is used for treating a subject with locally or regionally advanced squamous cell carcinoma of the head and neck in combination with radiation therapy. In other aspects, the p97-cetuximab conjugate is used for treating a subject with recurrent locoregional disease or metastatic squamous cell carcinoma of the head and neck in combination with platinum-based therapy with 5-fluorouracil (5-FU). In some aspects, the p97-cetuximab conjugate is used in combination with irinotecan for treating a subject with EGFR-expressing colorectal cancer and that is refractory to irinotecan-based chemotherapy.

In some instances, the subject has or is at risk for having a lysosomal storage disease. Certain methods thus relate to the treatment of lysosomal storage diseases in a subject in need thereof, optionally those lysosomal storage diseases associated with the central nervous system. Exemplary lysosomal storage diseases include aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, Gaucher disease, globoid cell leucodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leucodystrophy, mucolipidosis type I, sialidosis types I/II mucolipidosis types II/III I-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB Morquio syndrome, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease types NB, Niemann-Pick disease, Niemann-Pick disease type C1, Niemann-Pick disease type C2, pycnodysostosis, Schindler disease types I/II, Schindler disease, and sialic acid storage disease. In these and related embodiments, the p97 polypeptide can be conjugated to one or more polypeptides associated with a lysosomal storage disease, as described herein.

In certain instances, the subject has or is at risk for having an auto-immune disorder and/or a neurodegenerative or other neurological disorder, optionally of the CNS. Hence, also included are methods of treating a degenerative or autoimmune disorder of the central nervous system (CNS) in a subject in need thereof. For instance, in specific embodiments, the degenerative or autoimmune disorder of the CNS is Alzheimer's disease, Huntington's disease, Parkinson's disease, or multiple sclerosis (MS). Hence, certain embodiments include administering a p97 conjugate to a subject having Alzheimer's disease, Huntington's disease, Parkinson's disease, or MS. In particular embodiments, the p97 polypeptide is conjugated to an antibody or other agent that specifically binds to amyloid-β (e.g., $A\beta_{(1-42)}$ or tumor necrosis factor (TNF-α, TNF-β) for Alzheimer's Disease, Huntingtin for Huntington's Disease, α-synuclein for Parkinson's Disease, or α4 integrin, CD25, or IL-23 for MS. In particular embodiments, the p97 polypeptide is conjugated to an antibody or other agent that specifically binds to tumor necrosis factor (TNF-α, TNF-β) for the treatment of other neurological conditions such as stroke, traumatic brain injury (TBI), spinal stenosis, acute spinal cord injury, or spinal cord compression. In some embodiments, the p97 polypeptide is conjugated to an interferon-β polypeptide or an antibody that specifically binds to the alpha-subunit of the IL-2 receptor (CD25), α4 integrin, CD20, CD52, IL-12, IL-23, the p40 subunit of IL-12 and IL-23, or at least one of the axonal regrowth and remyelination inhibitors Nogo-A and LINGO-1, for the treatment of MS. In specific embodiments, the p97 polypeptide is conjugated to daclizumab, natalizumab, rituximab, ocrelizumab, ofatumumab, alemtuzumab, or ustekinumab (CNTO 1275), for the treatment of MS.

Also included are methods of treating pain in a subject in need thereof. General examples of pain include acute pain and chronic pain. In some instances, the pain has at least one CNS component. Specific examples of pain include nociceptive pain, neuropathic pain, breakthrough pain, incident pain, phantom pain, inflammatory pain including arthritic pain, or any combination thereof. In some aspects, the pain has a centrally-acting component, such as central pain syndrome (CPS), where the pain is associated with damage to or dysfunction of the CNS, including the brain, brainstem, and/or spinal cord.

In particular instances, the pain is nociceptive pain, optionally visceral, deep somatic, or superficial somatic pain. Nociceptive pain is usually caused by stimulation of peripheral nerve fibers that respond to stimuli approaching or exceeding harmful intensity (nociceptors), and may be classified according to the mode of noxious stimulation; for example, "thermal" (e.g., heat or cold), "mechanical" (e.g., crushing, tearing, cutting) and "chemical." Visceral structures are highly sensitive to stretch, ischemia and inflammation, but relatively insensitive to other stimuli such as burning and cutting. Visceral pain is most often diffuse, difficult to locate, and is sometimes referred to as having a distant, or superficial, structure. Visceral pain can be accompanied by nausea and vomiting, and is sometimes described as sickening, deep, squeezing, and dull. Deep somatic pain is usually initiated by the stimulation of nociceptors in ligaments, tendons, bones, blood vessels, fasciae and muscles, and is often characterized as a dull, aching, or poorly localized pain. Examples include sprains and broken bones. Superficial pain is mainly initiated by activation of nociceptors in the skin or other superficial tissue, and is sharp, well-defined and clearly located. Examples of injuries that produce superficial somatic pain include wounds and burns.

Neuropathic pain results from damage or disease affecting the somatosensory system. It may be associated with abnormal sensations called dysesthesia, and pain produced by normally non-painful stimuli (allodynia). Neuropathic pain may have continuous and/or episodic (paroxysmal) components, the latter being compared to an electric shock. Common characteristics of neuropathic pain include burning or coldness, "pins and needles" sensations, numbness, and itching. Neuropathic pain may result from disorders of the peripheral nervous system or the central nervous system (e.g., brain, spinal cord). Neuropathic pain may be characterized as peripheral neuropathic pain, central neuropathic pain, or mixed (peripheral and central) neuropathic pain.

Central neuropathic pain is found in spinal cord injury, multiple sclerosis, and strokes. Additional causes of neuropathic pain include diabetic neuropathy, herpes zoster infection, HIV-related neuropathies, nutritional deficiencies, toxins, remote manifestations of malignancies, immune mediated disorders, and physical trauma to a nerve trunk. Neuropathic pain also associates with cancer, mainly as a direct result of a cancer or tumor on peripheral or central nerves (e.g., compression by a tumor), or as a side effect of chemotherapy, radiation injury, or surgery.

In some instances, the pain is breakthrough pain. Breakthrough pain is pain that comes on suddenly for short periods of time and is not alleviated by the subject's normal pain management regimen. It is common in cancer patients who often have a background level of pain controlled by medications, but whose pain periodically "breaks through" the medication. Hence, in certain instances, the subject is taking pain medication, and is optionally a subject with cancer pain, e.g., neuropathic cancer pain.

In certain instances, the pain is incident pain, a type of pain that arises as a result of an activity. Examples include moving an arthritic or injured joint, and stretching a wound.

In specific instances, the pain is osteoarthritis, low back pain (or lumbago), including acute, sub-acute, and chronic low back pain (CLBP), bone cancer pain, or interstitial cystitis.

Osteoarthritis (OA), also referred to as degenerative arthritis or degenerative joint disease or osteoarthrosis, is a group of mechanical abnormalities involving degradation of joints, including articular cartilage and subchondral bone. Symptoms of OA may include joint pain, tenderness, stiffness, locking, and sometimes an effusion. OA may be initiated by variety of causes, including hereditary, developmental, metabolic, and mechanical causes, most of which lead to the loss of cartilage. When bone surfaces become less well protected by cartilage, bone may be exposed and damaged. As a result of decreased movement secondary to pain, regional muscles may atrophy, and ligaments may become increasingly lax. Particular examples include osteoarthritis of the knee, and osteoarthritis of the hip.

Interstitial cystitis, or bladder pain syndrome, is a chronic, oftentimes severely debilitating disease of the urinary bladder. Of unknown cause, it is characterized, for instance, by pain associated with the bladder, pain associated with urination (dysuria), urinary frequency (e.g., as often as every 10 minutes), urgency, and/or pressure in the bladder and/or pelvis.

In particular methods for treating pain, the p97 polypeptide is conjugated to an antibody or other agent that specifically binds to NGF or TrkA. In specific embodiments, the p97 polypeptide is conjugated to tanezumab for the treatment of pain, optionally for the treatment of osteoarthritis of the knee or hip, chronic low back pain, bone cancer pain, or interstitial cystitis.

Certain embodiments include combination therapies for treating pain. For instance, a subject with pain may be administered a p97-antibody conjugate described herein, where the antibody specifically binds to at least one pain-associated antigen, in combination with one or more pain medications, including analgesics and anesthetics. Exemplary analgesics include, without limitation, paracetamol/acetaminophen; non-steroidal anti-inflammatory drugs (NSAIDS) such as salicylates (e.g., aspirin), propionic acid derivatives (e.g., ibuprofen, naproxen), acetic acid derivatives (e.g., indomethacin), enolic acid derivatives, fenamic acid derivatives, and selective COX-2 inhibitors; opiates/opioids and morphinomimetics such as morphine, buprenorphine, codeine, oxycodone, oxymorphone, hydrocodone, dihydromorphine, dihydrocodeine, levorphanol, methadone, dextropropoxyphene, pentazocine, dextromoramide, meperidine (or pethidin), tramadol, noscapine, nalbuphine, pentacozine, papverine, papaveretum, alfentanil, fentanyl, remifentanil, sufentanil, and etorphine; and other agents, such as flupirtine, carbamazepine, gabapentin, and pregabalin, including any combination of the foregoing.

As noted above, certain subjects are about to undergo, are undergoing, or have undergone therapy with an otherwise cardiotoxic agent, that is, an agent that displays cardiotoxicity in its unconjugated form (an agent that is not conjugated to p97). Such subjects can benefit from administration of a p97-agent conjugate, relative to administration of the agent alone, partly because p97 can exert a cardioprotective effect on otherwise cardiotoxic agents by a mechanism that is believed to differ from its BBB transport properties. Hence, such subjects can be treated with a p97-cardiotoxic agent conjugate for a variety of disease conditions, including diseases of the CNS described herein, and diseases relating to peripheral, non-CNS tissues.

Exemplary cardiotoxic agents are described elsewhere herein, and can be identified according to well-known in vivo diagnostic and in vitro screening techniques. See Bovelli et al., 2010, supra; Inoue et al., *AATEX* 14, Special Issue, 457-462, 2007; and Dorr et al., *Cancer Research*. 48:5222-5227, 1988.

For instance, subjects undergoing therapy with a suspected cardiotoxic agent can be monitored by imaging techniques to asses LV systolic and diastolic dysfunction, heart valve disease, pericarditis and pericardial effusion, and carotid artery lesions. LV fractional shortening and LVEF are the most common indexes of LV systolic function for cardiac function assessment, for instance, during chemotherapy. Also, Doppler-derived diastolic indexes represent an early sign of LV dysfunction in patients undergoing therapy, so that evaluation of mitral diastolic flow pattern, early peak flow velocity to atrial peak flow velocity (E/A) ratio, deceleration time of E wave and isovolumic relaxation time can be useful to detect diastolic changes of LV function before systolic dysfunction occurs. Pulsed tissue Doppler may be performed during a standard Doppler echocardiographic examination; it can be reliable in providing quantitative information on myocardial diastolic relaxation and systolic performance (E' wave, A' wave and S wave velocity). Tissue Doppler of LV lateral mitral annulus has a recognized prognostic role and, in combination with PW Doppler of mitral inflow, provides accurate information about the degree of LV filling pressure. Early changes in LV myocardial function have been identified by pulsed tissue Doppler of multiple LV sites, and can be relevant determinants of cardiotoxicity.

In particular embodiments, the cardiotoxic agent is a chemotherapeutic, and the subject has cancer. Specific examples of cancers include, without limitation, breast cancers, prostate cancers, gastrointestinal cancers, lung cancers, ovarian cancers, testicular cancers, head and neck cancers, stomach cancers, bladder cancers, pancreatic cancers, liver cancers, kidney cancers, squamous cell carcinomas, CNS or brain cancers (described herein), melanomas, non-melanoma cancers, thyroid cancers, endometrial cancers, epithelial tumors, bone cancers, and hematopoietic cancers.

In specific embodiments, the subject has a Her2/neu-expressing cancer, such as a breast cancer, ovarian cancer, stomach cancer, aggressive uterine cancer, or metastatic cancer, such as a metastatic CNS cancer, and the p97 polypeptide is conjugated to trastuzumab. Such patients can benefit not only from the therapeutic synergism resulting from the combination of p97 and trastuzumab, especially for CNS cancers, but also from the reduced cardiotoxicity of trastuzumab, resulting from the potential cardioprotective effects of p97.

As noted above, exemplary diseases that can be treated, ameliorated or prevented using the methods of the present invention include, but are not limited to the following: various cancers, neurological conditions, conditions involving disturbances in iron metabolism, Mucopolysaccharidosis I (MPS I), MPS II, MPS IIIA, MPS IIIB, Metachromatic Leukodystropy (MLD), Krabbe, Pompe, CLN2, Tay-Sachs, Niemann-Pick A and B, and other lysosomal diseases. For each disease the conjugated agent would comprise a specific compound, protein or enzyme. For methods involving MPS I, the preferred compound or enzyme is α-L-iduronidase. For methods involving MPS II, the preferred compound or enzyme iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is Arylsulfatase A. For methods involving Krabbe, the preferred compound or enzyme is Galactosylceramidase. For methods involving Pompe, the preferred compound or enzyme is acid-alpha-glucosidase. For methods involving CLN, the preferred compound or enzyme is thioesterase. For methods involving Tay-Sachs, the preferred compound or enzyme is hexosaminidase A. For methods involving Niemann-Pick A and B the preferred compound or enzyme is Acid Spingomyelinase. For methods involving other Glycogenosis disorders the preferred compound or enzyme is glycolipidoses, mucopolysaccharidoses, oligosaccharidoses.

The p97 fragment-conjugates of the present invention can be administered with a "pharmaceutically acceptable carrier." Such carriers encompass any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result on a health condition, pathology, disease of a subject or for a diagnostic purpose. The desired result may comprise a subjective or objective improvement in the recipient of the dosage.

A "prophylactic treatment" is a treatment administered to a subject who does not exhibit signs of a disease or exhibits only early signs of a disease, wherein treatment is administered for the purpose of decreasing the risk of developing a pathology. The conjugate conjugates of the invention may be given as a prophylactic treatment.

A "therapeutic treatment" is a treatment administered to a subject who exhibits signs of pathology, wherein treatment is administered for the purpose of diminishing or eliminating those pathological signs. The signs may be subjective or objective.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a p97 fragment-agent conjugate of the present invention and a pharmaceutically acceptable carrier.

The term "pharmaceutical composition" indicates a composition suitable for pharmaceutical use in a subject, including an animal or human. A pharmaceutical composition generally comprises an effective amount of the p97 fragment-conjugate and a pharmaceutically acceptable carrier.

The conjugates may be administered by a variety of routes. For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The p97 fragment-agent conjugates can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The p97 fragment-agent conjugates can be utilized in aerosol formulation to be administered via inhalation. The conjugates of the present invention can be formulated into pressurized acceptable propellants such as dichlorodifluoromethane, propane, nitrogen and the like.

Furthermore, the p97 fragment-agent conjugates can be made into suppositories by mixing with a variety of bases such as emulsifying bases or water-soluble bases. The conjugates of the present invention can be administered rectally via a suppository. The suppository can include vehicles such as cocoa butter, carbowaxes and polyethylene glycols, which melt at body temperature, yet are solidified at room temperature.

Unit dosage forms of the p97 fragment-agent conjugates for oral or rectal administration as, for instance, syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the conjugate in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of conjugates of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

In practical use, the conjugates according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

With respect to transdermal routes of administration, methods for transdermal administration of drugs are disclosed in Remington's Pharmaceutical Sciences, 17th Edition, (Gennaro et al. Eds., Mack Publishing Co., 1985). Dermal or skin patches are a preferred means for transdermal delivery of the p97 fragment-agent conjugates of the invention. Patches preferably provide an absorption enhancer such as DMSO to increase the absorption of the conjugates. Other methods for transdermal drug delivery are disclosed in U.S. Pat. Nos.

5,962,012, 6,261,595, and 6,261,595. Each of which is incorporated by reference in its entirety.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific agent, the severity of the symptoms and the susceptibility of the subject to side effects. Preferred dosages for a given conjugate are readily determinable by those of skill in the art by a variety of means.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

In practical use, the conjugates according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. The percentage of an active agent in these compositions may, of course, be varied and may conveniently be between about 2 percent to about 60 percent of the weight of the unit.

The conjugates of the invention are useful for therapeutic, prophylactic and diagnostic intervention in animals, and in particular in humans.

Compositions of the present invention may be administered encapsulated in or attached to viral envelopes or vesicles. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer conjugates intracellularly and to deliver the conjugates to the target organs. Controlled release of a p97-composition of interest may also be achieved using encapsulation (see, e.g., U.S. Pat. No. 5,186,941).

In certain aspects, the p97 polypeptide sequence and the agent are each, individually or as a pre-existing conjugate, bound to or encapsulated within a particle, e.g., a nanoparticle, bead, lipid formulation, lipid particle, or liposome, e.g., immunoliposome. For instance, in particular embodiments, the p97 polypeptide sequence is bound to the surface of a particle, and the agent of interest is bound to the surface of the particle and/or encapsulated within the particle. In some of these and related embodiments, the p97 polypeptide and the agent are covalently or operatively linked to each other only via the particle itself (e.g., nanoparticle, liposome), and are not covalently linked to each other in any other way; that is, they are bound individually to the same particle. In other embodiments, the p97 polypeptide and the agent are first covalently or non-covalently conjugated to each other, as described herein (e.g., via a linker molecule), and are then bound to or encapsulated within a particle (e.g., immunoliposome, nanoparticle). In specific embodiments, the particle is a liposome, and the composition comprises one or more p97 polypeptides, one or more agents of interest, and a mixture of lipids to form a liposome (e.g., phospholipids, mixed lipid chains with surfactant properties). In some aspects, the p97 polypeptide and the agent are individually mixed with the lipid/liposome mixture, such that the formation of liposome structures operatively links the p97 polypeptide and the agent without the need for covalent conjugation. In other aspects, the p97 polypeptide and the agent are first covalently or non-covalently conjugated to each other, as described herein, and then mixed with lipids to form a liposome. The p97 polypeptide, the agent, or the p97-agent conjugate may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents, such as cytotoxic agents.

Any route of administration which brings the conjugates into contact with the target cells, tissue or organ may be used. The conjugates can be administered peripherally or centrally. The conjugates may also be administered intravenously or by intraperitoneally. The conjugates may be administered locally or regionally.

The dosages to be administered will depend on individual needs and characteristics (age, weight, severity of condition, on the desired effect, the active agent used, and the chosen route of administration and treatment regimen). Preferred dosages of p97 fragment-conjugates range from about 0.02 pmol/kg to about 2.5 nmol/kg, and particularly preferred dosages range from 2-250 pmol/kg; alternatively, preferred doses of the p97 fragment conjugate may be in the range of 0.02 to 2000 mg/kg. These dosages will be influenced by the number of agent moieties associated with each p97 fragment molecule. In addition, dosages may be calculated based on the agent to be administered and the severity of the condition to be treated. Empirical and theoretical methods for determining dose response relationships and optimizing the dosages employed an individual patients therapy are will known to one of ordinary skill in the art.

The p97 fragment-conjugates of the invention are, for example, useful for therapeutic and prophylactic intervention the treatment of lysosomal storage diseases in animals, and in particular in humans. The subject methods find use in the treatment of a variety of different lysosomal storage diseases. In certain embodiments, of particular interest is the use of the subject methods in disease conditions where an active agent having desired activity has been previously identified, but in which the active agent is not adequately targeted to the target site, area or compartment. With such active agent, the subject methods can be used to enhance the therapeutic efficacy and therapeutic index of active agent.

The p97 fragment-conjugates of the invention are, for example, useful for delivering therapeutic or diagnostic agents across the blood brain barrier.

Treatment is meant to encompass any beneficial outcome to a subject associated with administration of a conjugate including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the severity of the disease or in a magnitude of a parameter representative of the severity or presence of the disease, e.g., tissue damage, cell death, excess or harmful amounts of lysosomal storage materials, symptoms, associated with the pathological condition being treated, such as inflammation and pain associated therewith. As such, treatment also includes, but is not limited to, situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

A variety of hosts or subjects are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts or subjects will be humans.

Methods for identifying subjects with one or more of the diseases or conditions described herein are known in the art.

Also included are methods for imaging an organ or tissue component in a subject, comprising (a) administering to the subject a composition comprising a human p97 (melanotransferrin) polypeptide, or a variant thereof, where the p97 polypeptide is conjugated to a detectable entity, and (b) visualizing the detectable entity in the subject, organ, or tissue.

In particular embodiments, the organ or tissue compartment comprises the central nervous system (e.g., brain, brainstem, spinal cord). In specific embodiments, the organ or tissue compartment comprises the brain or a portion thereof, for instance, the parenchyma of the brain.

A variety of methods can be employed to visualize the detectable entity in the subject, organ, or tissue. Exemplary non-invasive methods include radiography, such as fluoroscopy and projectional radiographs, CT-scanning or CAT-scanning (computed tomography (CT) or computed axial tomography (CAT)), whether employing X-ray CT-scanning, positron emission tomography (PET), or single photon emission computed tomography (SPECT), and certain types of magnetic resonance imaging (MRI), especially those that utilize contrast agents, including combinations thereof.

Merely by way of example, PET can be performed with positron-emitting contrast agents or radioisotopes such as $^{18}F$, SPECT can be performed with gamma-emitting contrast agents or radioisotopes such as $^{201}Tl$, $^{99m}TC$, $^{123}I$, and $^{67}Ga$, and MRI can be performed with contrast agents or radioisotopes such as $^{3}H$, $^{13}C$, $^{19}F$, $^{17}O$, $^{23}Na$, $^{31}F$, and $^{129}Xe$, and Gd (gadolidinium; chelated organic Gd (III) complexes). Any one or more of these exemplary contrast agents or radioisotopes can be conjugated to or otherwise incorporated into a p97 polypeptide and administered to a subject for imaging purposes. For instance, p97 polypeptides can be directly labeled with one or more of these radioisotopes, or conjugated to molecules (e.g., small molecules) that comprise one or more of these radioisotopic contrast agents, or any others described herein.

EXAMPLES

Example 1

Human P97 Digestion with Hydroxylamine

Even though previous studies have shown that soluble MTf is capable of delivering iron, paclitaxel and adriamycin across the BBB into the brain, it was desired to determine if a smaller version of soluble MTf was able to retain its ability to cross the BBB and function more efficiently.

By analyzing the sequence of soluble MTf (see FIG. 1; residues 20-709 of full-length human MTf), it was determined that hydroxylamine, an inorganic compound, could shorten the soluble MTf sequence significantly without affecting its iron binding site. One of the resulting fragments of MTf is approximately 60-70 KDa in size (see FIG. 2). Complete digestion of soluble MTf with hydroxylamine was predicted to result in four fragments (~60-70 KDa, ~2.5 KDa, ~5.5 KDa, and ~5.8 KDa), the sizes of which are based on expected migration in a 1-D SDS-PAGE gel. Completely digested fragments of soluble MTf include amino acid residues 1-564 (SEQ ID NO:1), residues 565-586 (SEQ ID NO:2), residues 587-637 (SEQ ID NO:3), and residues 638-390 (SEQ ID NO:4).

Partially digested fragments are also predicted. For instance, partially digested fragments of soluble MTf include amino acid residues 1-586 (SEQ ID NO:5), residues 1-637 (SEQ ID NO:6), residues 565-637 (SEQ ID NO:7), residues 565-690 (SEQ ID NO:8), and residues 587-690 (SEQ ID NO:9).

The digestion was performed by dissolving 5 g hydroxylamine hydrochloride (sigma: 255580) in 5M NaOH. The pH was adjusted to 9.0. Human p97 was mixed with hydroxylamine solution, at a final concentration of 2.4M hydroxylamine. The mixture was incubated for 2-3 days at 42° C. The reaction was terminated by adding 0.1 volume of acetic acid or acidifying the mixture to PH 4.5 with glacial acetic acid. The mixture was cooled to 4° C. It was then dialyzed against 5% acetic acid O/N. Next it was dialyzed against PBS O/N.

Example 2

Bio-Distribution and Pharmacokinetics of the P97 60 KD Fragment

Figure 3:
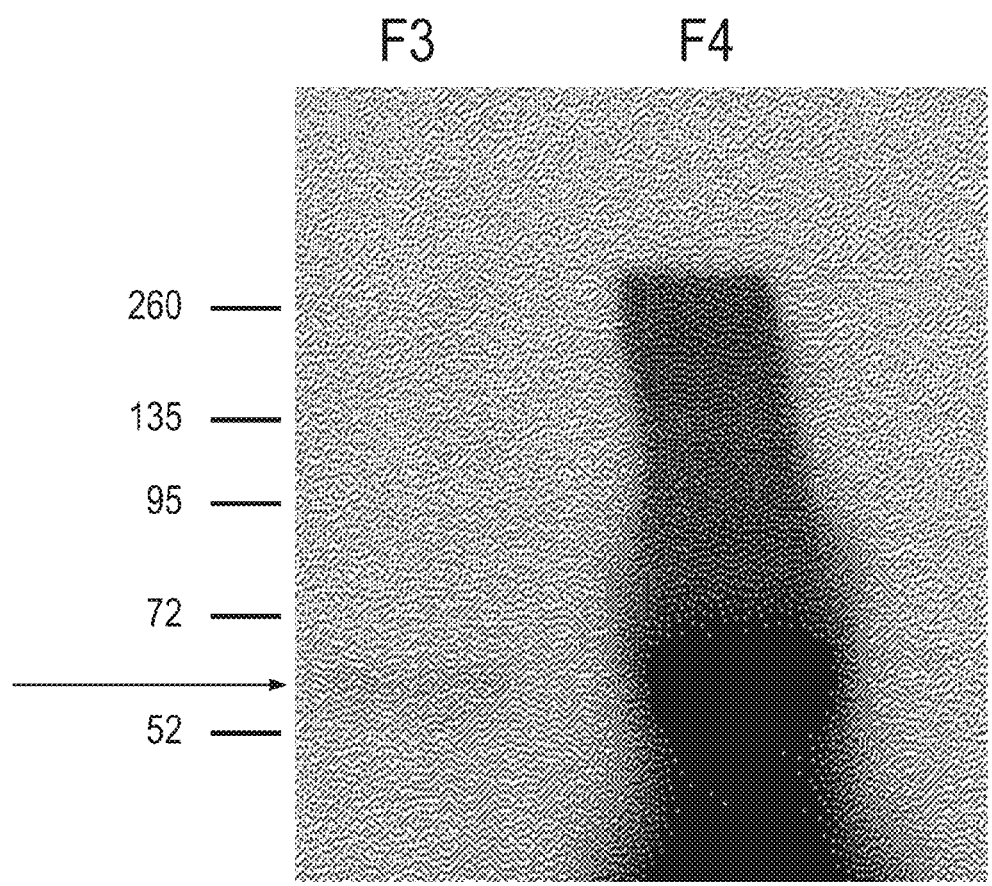
FIG. 3 is a blot that shows the iodinated human p97 fragment (60 kDa).
Figure 4:
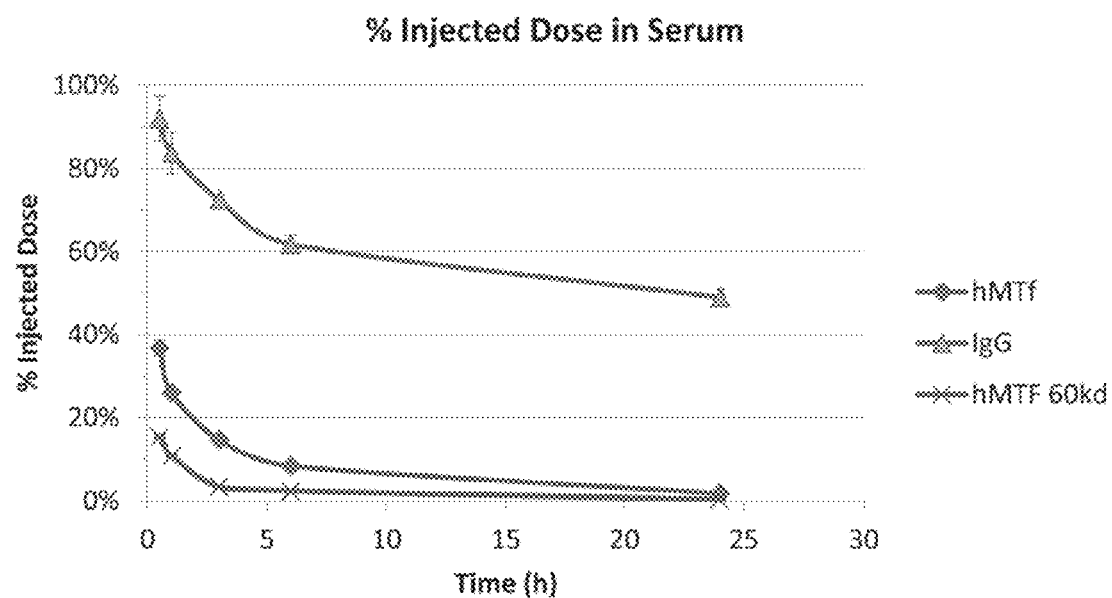
FIG. 4 is a line graph that shows the percentage of $^{125}$I radiolabeled p97 fragment present in the serum following delivery into mice through tail vein injection.

In order to determine if the p97 fragment retained the ability of the full length p97 to cross the BBB, the 60 kDa MTf fragment was radiolabeled with $^{125}I$ and delivered into the mice through tail vein injection (FIG. 3). The bio-distribution and pharmacokinetics studies described herein show that MTf fragment was able to be absorbed rapidly from the serum similar to MTf, while significant amount of IgG remained in the circulation after the first 0.5 hour (FIG. 4).

Figure 5:
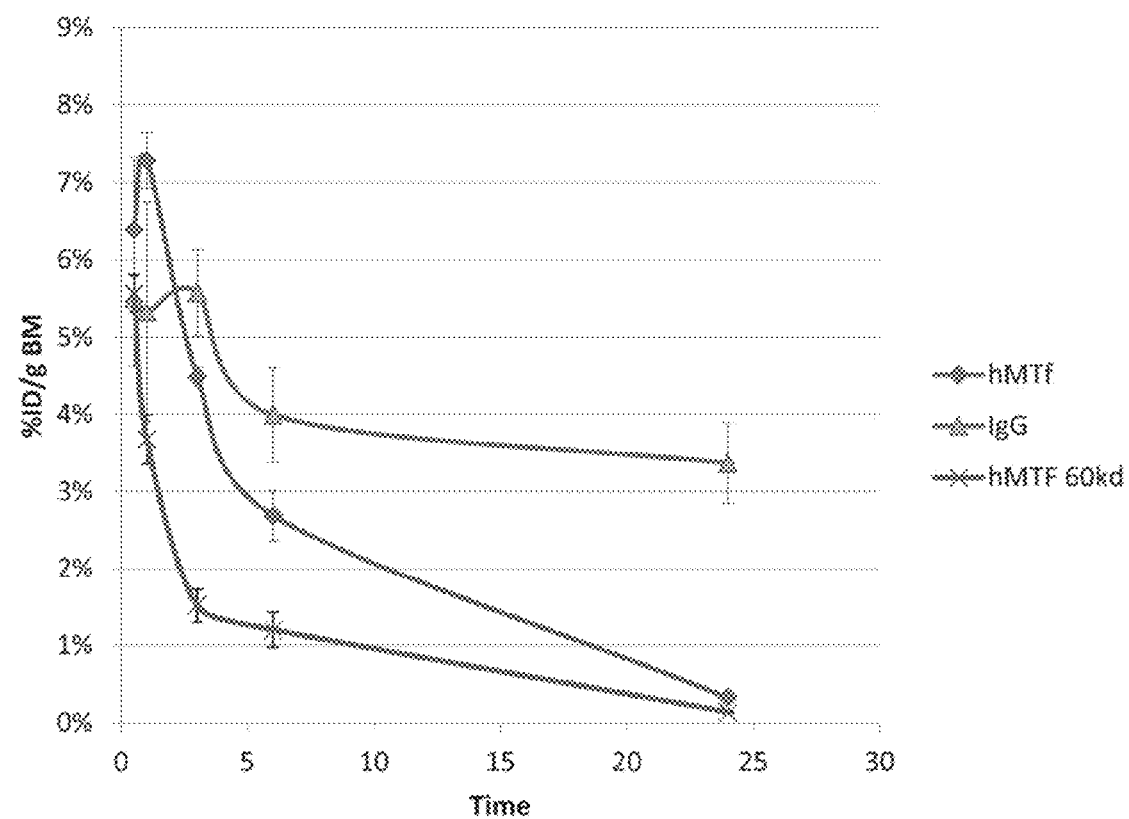
FIG. 5 is a line graph that shows the percentage of the injected dose of p97 fragment normalized to body mass (% ID/g BM) present in the brain over time.
Figure 6:
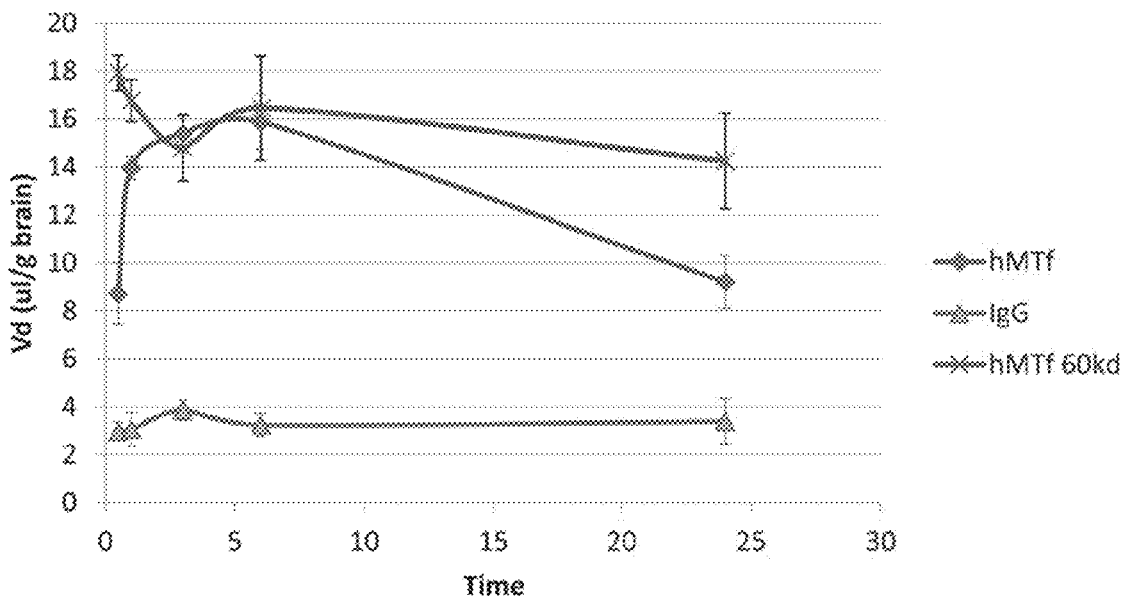
FIG. 6 is a line graph that shows the ratio between radioactive counts (CPM) in one gram of tissue relative to one microliter of serum (Vd) in the brain over time.
Figure 7:
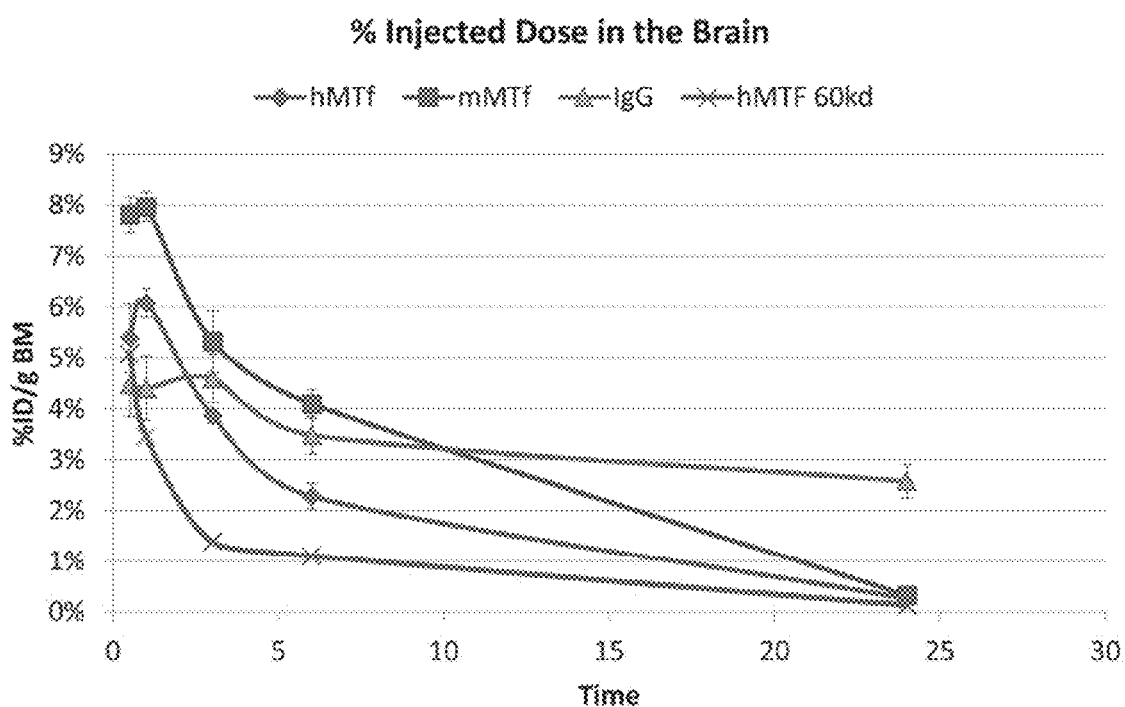
FIG. 7 is a line graph that shows the percent of the injected dose of p97 fragment in the brain over 24 hours.
Figure 8:
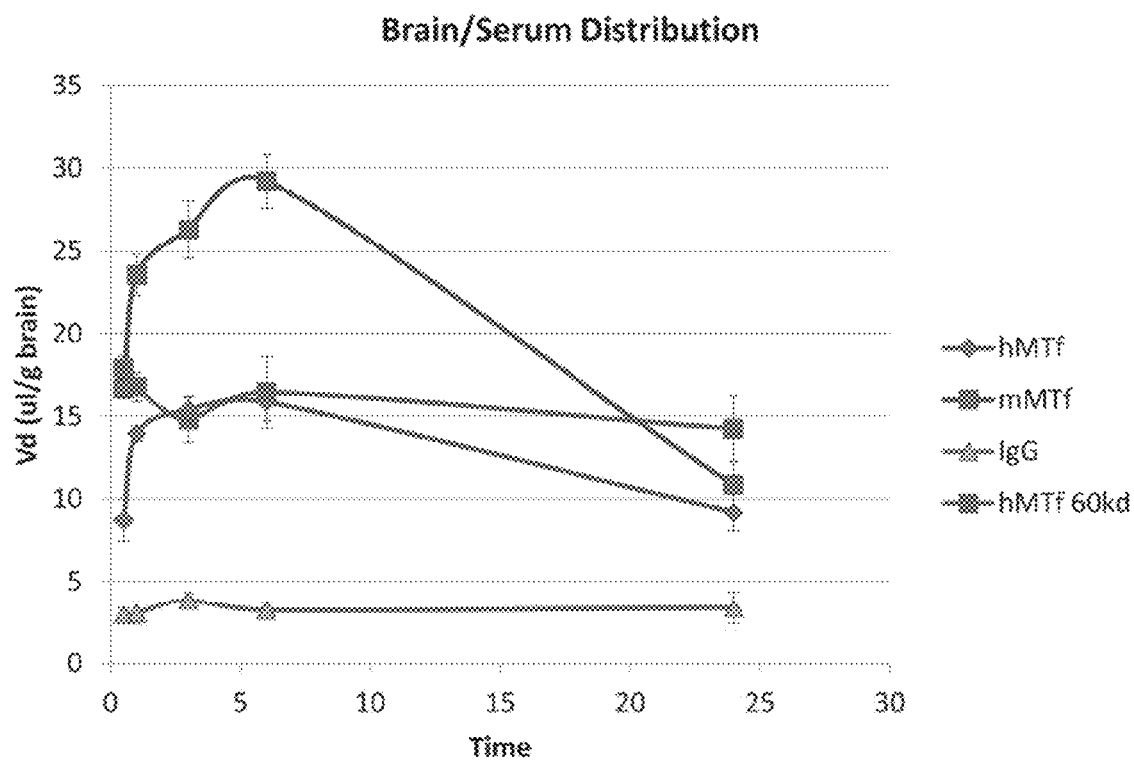
FIG. 8 is a line graph that shows the ratio between p97 fragment present in the brain relative to serum over 24 hours.
Figure 9:
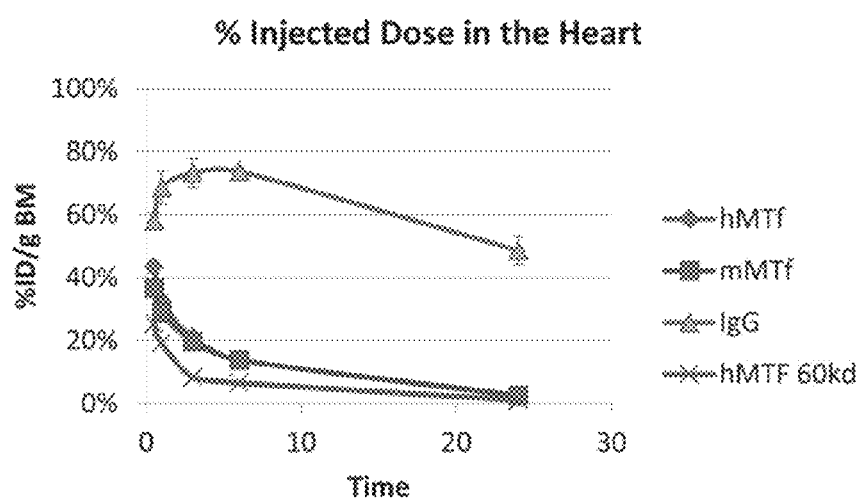
FIG. 9 is a line graph that shows the percent of the injected dose of p97 fragment in the heart over 24 hours.
Figure 10:
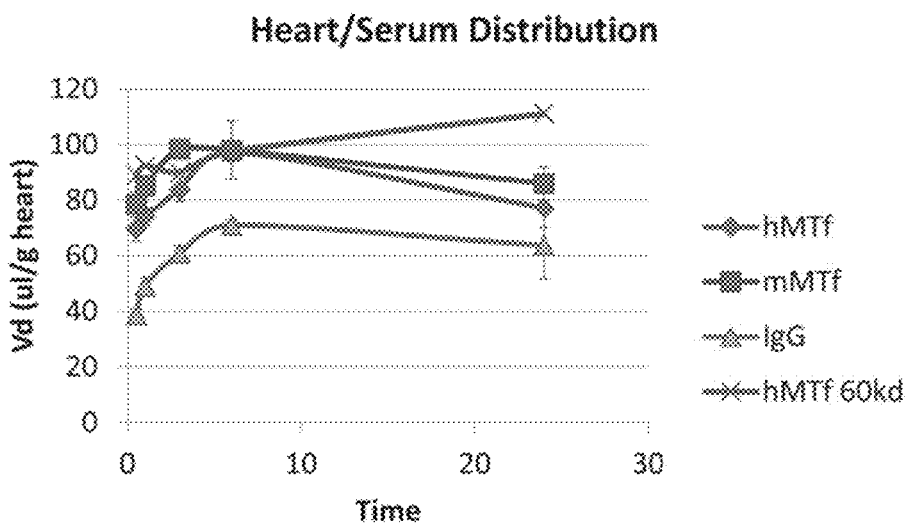
FIG. 10 is a line graph that shows the ratio between p97 fragment present in the heart relative to serum over 24 hours.
Figure 11:
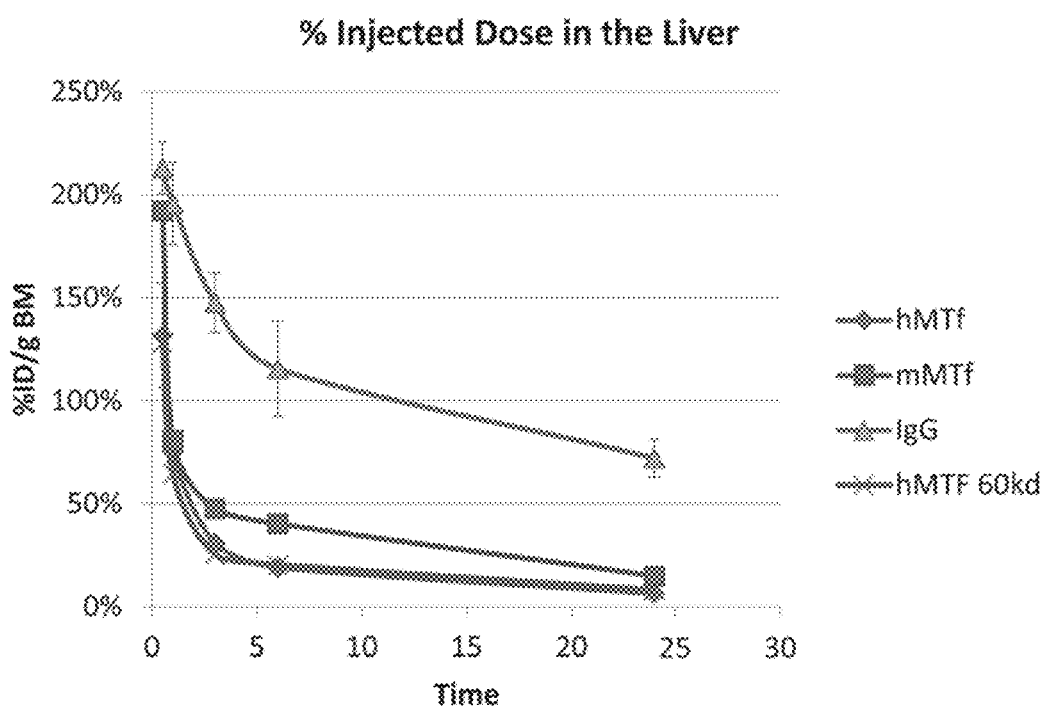
FIG. 11 is a line graph that shows the percent of the injected dose of p97 fragment in the liver over 24 hours.
Figure 12:
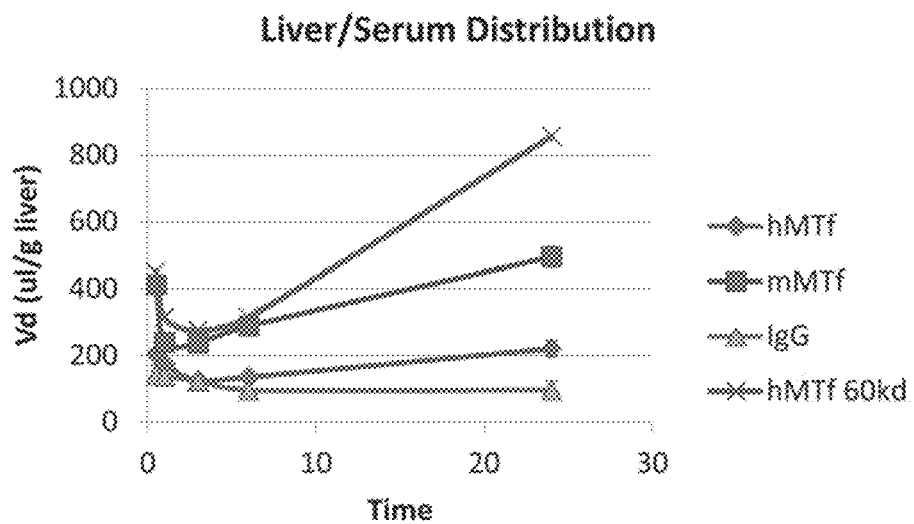
FIG. 12 is a line graph that shows the ratio between p97 fragment present in the liver relative to serum over 24 hours.
Figure 13:
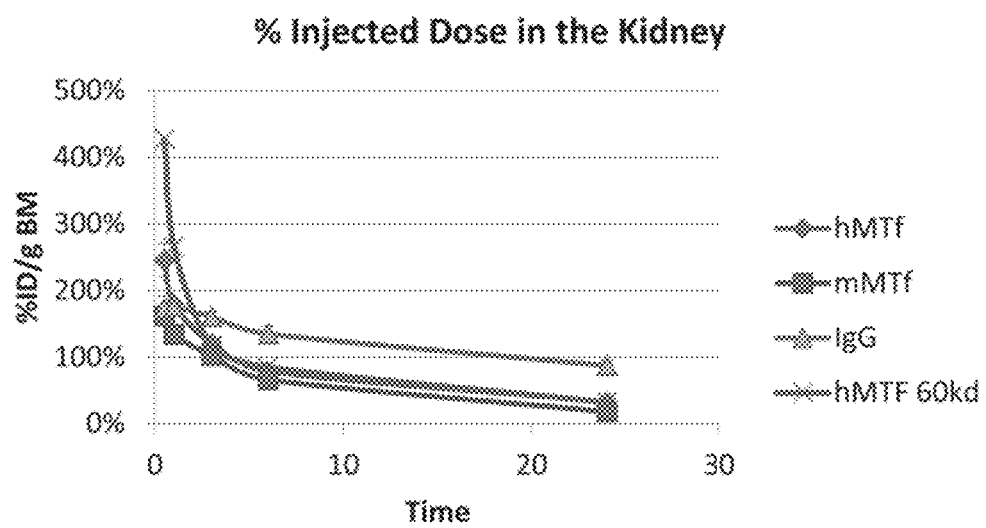
FIG. 13 is a line graph that shows the percent of the injected dose of p97 fragment in the kidney over 24 hours.
Figure 14:
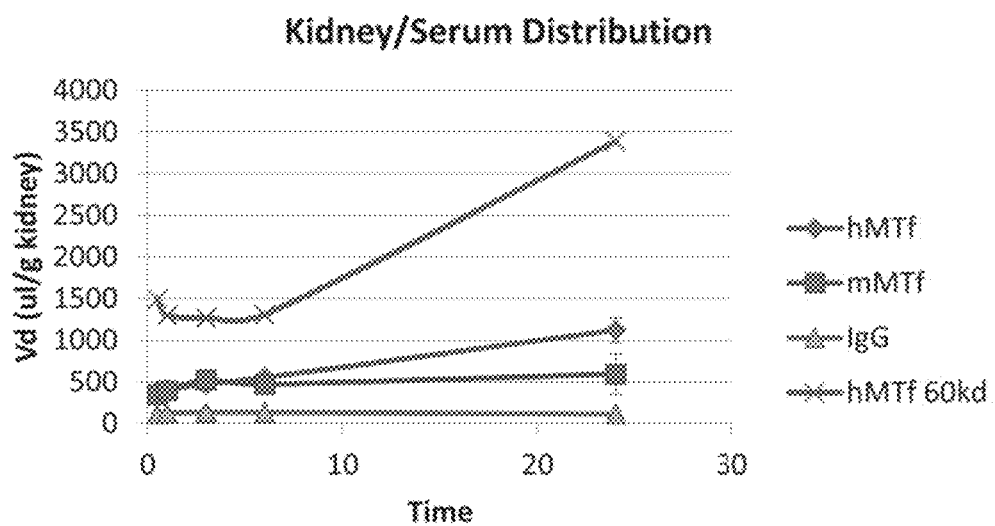
FIG. 14 is a line graph that shows the ratio between p97 fragment present in the kidney relative to serum over 24 hours.
Figure 15:
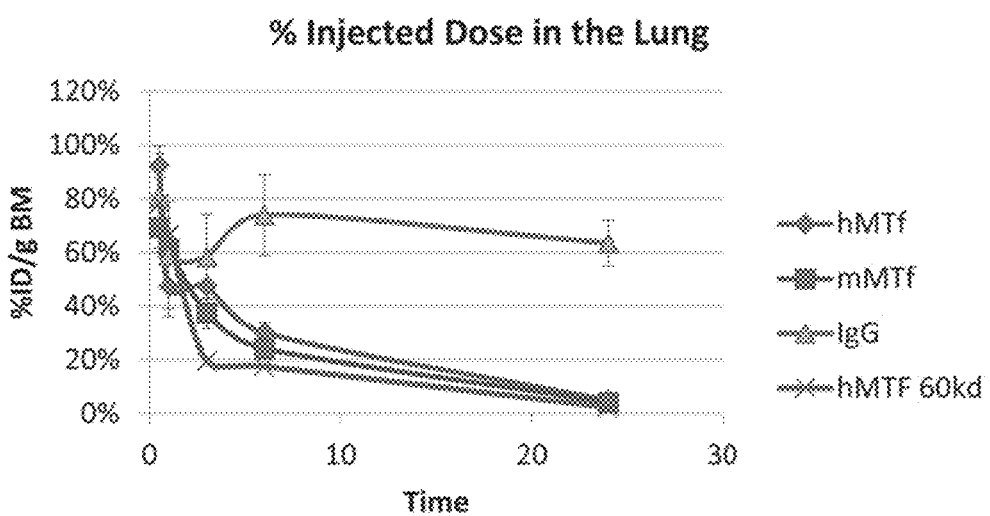
FIG. 15 is a line graph that shows the percent of the injected dose of p97 fragment in the lung over 24 hours.
Figure 16:
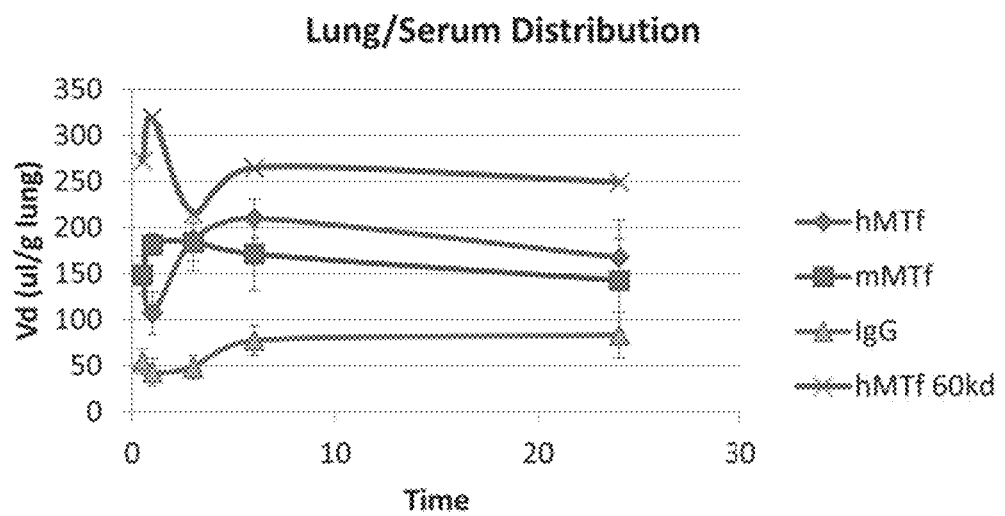
FIG. 16 is a line graph that shows the ratio between p97 fragment present in the lung relative to serum over 24 hours.
Figure 17:
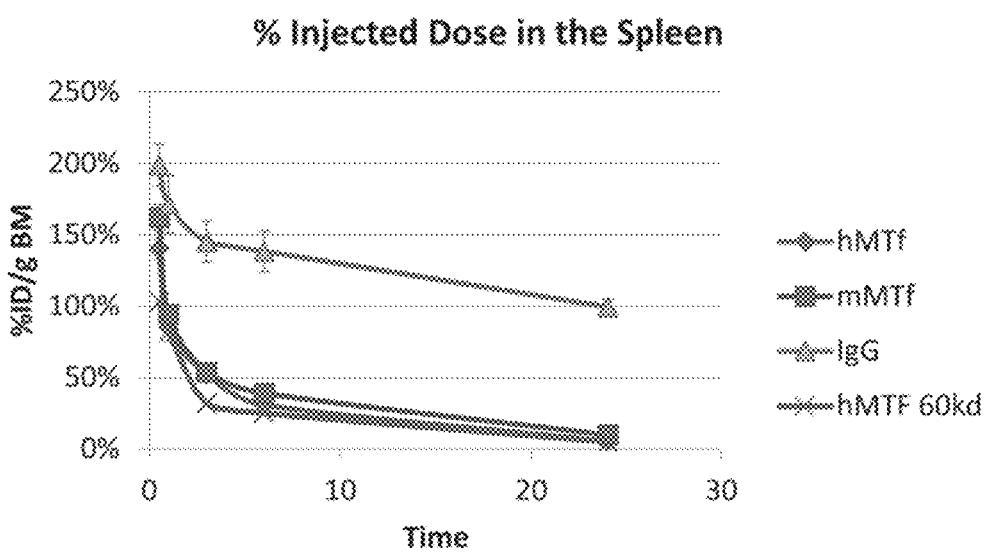
FIG. 17 is a line graph that shows the percent of the injected dose of p97 fragment in the spleen over 24 hours.
Figure 18:
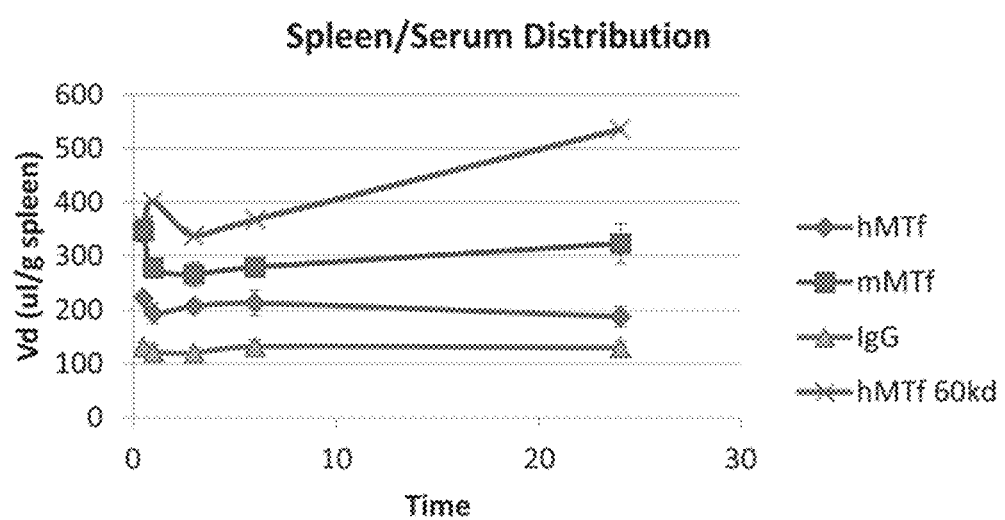
FIG. 18 is a line graph that shows the ratio between p97 fragment present in the spleen relative to serum over 24 hours.

The brain distribution of MTf, MTf fragment and IgG control was analyzed over 24 hour time period after a single I.V. injection. The data is presented as the percentage of injected dose normalized to body mass (% ID/g BM; FIG. 5), as well as the ratio between radioactive counts (CPM) in one gram of tissue relative to one microliter of serum (Vd; FIG. 6). These results demonstrated that MTf fragment follow a similar profile as MTf with a gradual decrease over the 24 hour time period. When the distribution of MTf, MTf fragment and IgG were normalized to the levels in the serum (Vd), the results showed that both MTf and MTf fragment distributed to the brain 5× higher that of IgG. Taken together, these data suggest that MTf fragment is able to cross the BBB and accumulate in the brain similar to that of MTf. Similar analyses were performed studying the heart, liver, kidney, lung and spleen, as shown in FIGS. 9-18.

These results strongly suggest that MTf fragments have potential as an alternative to full length or soluble MTf as a drug delivery carrier. One advantage to this would be to reduce the overall size of the carrier and the amount of protein per molecule of "therapeutic drug" that would have to be delivered in each therapeutic dose.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A conjugate, comprising a p97 polypeptide that consists of at least one of SEQ ID NO:1-8 or 9 or a sequence having at least 95% identity along its length to SEQ ID NO:1-8 or 9 or a sequence that differs from SEQ ID NO:1-8 or 9 by the addition or deletion of about 1, 2, 3, 4, 5, 6, 7, 8, 9, or 10 N-terminal and/or C-terminal residues, where the p97 polypeptide is covalently or operatively linked to (a) etanercept or an antigen-binding fragment or variant thereof that specifically binds to tumor necrosis factor (TNF)-α, or (b) an antibody or antigen-binding fragment thereof that specifically binds to amyloid-β(Aβ).

2. The conjugate of claim 1, where the p97 polypeptide is covalently or operatively linked to etanercept or an antigen-binding fragment or variant thereof that specifically binds to TNF-α.

3. The conjugate of claim 2, where the p97 polypeptide is covalently or operatively linked to etanercept.

4. The conjugate of claim 1, where the p97 polypeptide is covalently or operatively linked to an antibody or antigen-binding fragment thereof that specifically binds to amyloid-β(Aβ).

5. The conjugate of claim 4, where the antibody or antigen-binding fragment thereof specifically binds to Aβ$_{(1-42)}$.

6. The conjugate of claim 1, where the p97 polypeptide is covalently linked to (a) or (b).

7. The conjugate of claim 6, where the p97 polypeptide is covalently linked to (a) or (b) via a linker.

8. The conjugate of claim 7, where the linker comprises a polyethylene glycol.

9. The conjugate of claim 6, where the p97 polypeptide is fused to (a) or (b) to form a fusion protein.

10. The conjugate of claim 8, where the fusion protein comprises a peptide linker.

11. A pharmaceutical composition, comprising a conjugate of claim 1 and a pharmaceutically acceptable carrier.

12. A method of treating a subject in need thereof, comprising administering to the subject a pharmaceutical composition of claim 10.

13. The method of claim 11, for treating a degenerative or autoimmune disorder of the central nervous system (CNS).

14. The method of claim 12, where the degenerative or autoimmune disorder of the CNS is Alzheimer's disease, Huntington's disease, Parkinson's disease, or multiple sclerosis (MS).

15. The method of claim 11, for treating pain, or a nervous system or autoimmune disorder.

16. The method of claim 14, for treating Alzheimer's disease, stroke, traumatic brain injury (TBI), spinal stenosis, acute spinal cord injury, or spinal cord compression.

* * * * *